(12) United States Patent
Fortin et al.

(10) Patent No.: US 8,536,542 B2
(45) Date of Patent: Sep. 17, 2013

(54) FLOW CYTOMETRY ANALYSIS ACROSS OPTICAL FIBER

(75) Inventors: Michel Fortin, Lac-Beauport (CA); Alain Chandonnet, Québec (CA); Claude Pare, Saint-Augustin-de-Desmaures (CA)

(73) Assignee: Institut National d'Optique, Quebec (CA)

( * ) Notice: Subject to any disclaimer, the term of this patent is extended or adjusted under 35 U.S.C. 154(b) by 395 days.

(21) Appl. No.: 12/936,609

(22) PCT Filed: Apr. 13, 2010

(86) PCT No.: PCT/CA2010/000564
§ 371 (c)(1),
(2), (4) Date: Oct. 6, 2010

(87) PCT Pub. No.: WO2011/085465
PCT Pub. Date: Jul. 21, 2011

(65) Prior Publication Data
US 2011/0291025 A1  Dec. 1, 2011

Related U.S. Application Data

(63) Continuation-in-part of application No. 11/509,584, filed on Aug. 25, 2006.

(60) Provisional application No. 61/295,780, filed on Jan. 18, 2010.

(51) Int. Cl.
*G01N 21/64* (2006.01)
*G02B 6/42* (2006.01)

(52) U.S. Cl.
USPC ............... 250/458.1; 385/31; 385/39

(58) Field of Classification Search
USPC ............... 250/458.1, 461.2; 385/12
See application file for complete search history.

(56) References Cited

U.S. PATENT DOCUMENTS

| 4,149,867 A | 4/1979 | Akamatsu et al. |
| 4,667,830 A | 5/1987 | Nozaki, Jr. et al. |

(Continued)

FOREIGN PATENT DOCUMENTS

| CA | 2004250 | 6/1990 |
| CA | 2204865 | 4/1997 |

(Continued)

OTHER PUBLICATIONS

Shapiro et al., 1986, "Flow Cytometers Using Optical Waveguides in Place of Lenses for Specimen Illumination and Light Collection.", Cytometry, 7: 221-223.

(Continued)

*Primary Examiner* — Casey Bryant
(74) *Attorney, Agent, or Firm* — Norton Rose Fulbright LLP; Alexandre Daoust

(57) ABSTRACT

An apparatus and method for analyzing a fluid with particle analytes, where the fluid is fed through a passageway within an optical fiber and excitation light is guided by the optical fiber across the passageway and intersects the fluid therein. The optical core is made multimode and is adapted to shape the excitation light with a uniform spatial illumination over a cross-section of the optical core and the passageway is configured relative to the optical core such that the particle analytes are exposed to substantially equal excitation light while circulating in the passageway.

34 Claims, 20 Drawing Sheets

(56) References Cited

U.S. PATENT DOCUMENTS

| | | | |
|---|---|---|---|
| 4,702,598 A | 10/1987 | Bohmer | |
| 4,889,407 A | 12/1989 | Markle et al. | |
| 5,464,581 A | 11/1995 | Van den Engh | |
| 5,475,487 A * | 12/1995 | Mariella et al. | 356/336 |
| 5,483,469 A | 1/1996 | Van den Engh et al. | |
| 5,579,429 A | 11/1996 | Naum | |
| 5,602,039 A | 2/1997 | Van den Engh | |
| 5,643,796 A | 7/1997 | Van den Engh et al. | |
| 5,700,692 A | 12/1997 | Sweet | |
| 5,912,257 A | 6/1999 | Prasad et al. | |
| 6,097,870 A * | 8/2000 | Ranka et al. | 385/127 |
| 6,713,019 B2 | 3/2004 | Ozasa et al. | |
| 6,793,642 B2 | 9/2004 | Connelly et al. | |
| 7,324,724 B2 | 1/2008 | Lévesque et al. | |
| 7,639,909 B2 | 12/2009 | Murshid et al. | |
| 7,724,371 B2 * | 5/2010 | Nerin et al. | 356/436 |
| 2003/0098421 A1 | 5/2003 | Ho | |
| 2006/0192940 A1 | 8/2006 | Phi-Wilson | |
| 2007/0047868 A1 * | 3/2007 | Beaulieu et al. | 385/12 |
| 2007/0164562 A1 * | 7/2007 | Valaskovic et al. | 285/245 |
| 2009/0161107 A1 | 6/2009 | Nerin et al. | |

FOREIGN PATENT DOCUMENTS

| | | |
|---|---|---|
| CA | 2321782 | 9/1999 |
| CA | 2234053 | 11/1999 |
| CA | 2611565 | 3/2007 |
| CA | 2524111 | 4/2007 |
| WO | 9801071 | 1/1998 |
| WO | 2007022641 | 3/2007 |

OTHER PUBLICATIONS

He G.S. et al., 1995' "Two-photon-pumped cavity lasing in a dye-solution-filled hollow-fiber system.", Optics Letters, 20 (23): 2393-2395.

Yiou S. et al, 2005, "Stimulated Raman scattering in an ethanol core microstructured optical fiber.", Optics Express, 13 (12): 4786-4791.

\* cited by examiner

FLOW CYTOMETRY ANALYSIS ACROSS OPTICAL FIBER

CROSS-REFERENCE TO RELATED APPLICATIONS/PRIORITY CLAIM

This application is a national phase of PCT patent application serial number PCT/CA2010/000564 filed Apr. 13, 2010, designating the United States of America, now pending and is a continuation-in-part of U.S. patent application Ser. No. 11/509,584 filed Aug. 25, 2006, and claims priority of U.S. provisional patent application 61/295,780 filed Jan. 18, 2010; the specifications of which are hereby incorporated by reference.

TECHNICAL FIELD

The invention relates generally to the field of flow cytometry. More particularly, the invention relates to methods and systems for studying a fluid with particle analytes channeled within a passageway intersecting the light guided in an optical fiber.

BACKGROUND

Flow cytometry is a technique which allows one to analyze or to sort particle analytes in a fluid medium (e.g. a liquid or a gas). Such particle analytes include small bodies like cells and bacteria and other particles such as fluorescent beads. In flow cytometers of the prior art, a fluid containing the small bodies is added to a sheath fluid forced by hydrodynamic into a small interaction region of laminar flow where particles transit one at a time, and a laser is aimed at the interaction region. The laser light, after having crossed the interaction region and interacted with the particle analyte, is received and analyzed, which gives information about the light-interacting properties (e.g. side scattering, forward scattering, fluorescence, etc. . . . ) of particles flowing within the focused sheath fluid in the interaction region. Several parameters of the particles may be studied simultaneously (e.g. the structure of the particle, the dimension of the particle, etc.) by marking the particles to be analyzed with dyes and measuring both the fluorescence emitted by those dyed particles and the intensity of the laser light beam transmitted and scattered in different directions after it has interacted with the fluid. All of the above techniques require the intervention of a skilled technician. In particular, in the case of the prior art flow cytometry techniques, a skilled technician must adjust and precisely align the laser beam so that the laser beam may efficiently interact with the particles flowing through the small interaction sheath region.

An alternative to classical sheath flow cytometer is capillary-based flow cell cytometers where the particles under test are free flowing into a capillary and a laser is used to transversally interrogate the properties of the particle analytes transiting in the capillary (see U.S. Pat. No. 7,410,809 to Goix et al.). In such systems, no sheath fluid is added and the particles are not forced to transit one at a time through the light-particle interaction region. Therefore, to minimize the occurrence of multiple particles passing at the same time through the interrogating beam, the sample containing the analyte is more diluted and operated at a flow rate comparatively much slower than in a standard flow cytometer. The beam delivery system is however similar to the one used in a standard cytometer in that it is based on bulk optical elements shaping the interrogation beam and bringing it to the interaction region. In some instances, the collection of scattered light from the interaction region is optimized by using capillaries having complex cross-section shapes to help collecting and focusing light of interest used for the characterization of the flowing analytes (see U.S. Pat. No. 7,564,542 to Ilkov).

Known flow cytometers usually employ lasers as the light source. Although lasers are generally effective in producing focused beams of sufficient intensity to excite the particles of interest and hence generate detectable fluorescence, the use of lasers can have some drawbacks. For example, the types of lasers employed in many known flow cytometers are very expensive, and thus increase the overall cost of the system. Also, because the lasers emit very high intensity light, stray light from the laser beam can interfere with the fluorescent and scattered light emanating from the particles of interest, thus adversely affecting their measurement by creating undesirable noise in the detection channels. Collection of fluorescent and scattered light is thus complicated by such source of noise.

Another known constraint is related to the beam quality of the laser requiring tight focusing to illuminate the small laminar flow region of interest where only one particle is present at a time. Homogeneous illumination over a small region requires light of high spatial quality generally obtained by the use of additional optical elements (e.g. collimation and focusing lens, filtering pinholes, etc. . . . ) adding to the cost and bulkiness of the beam delivery system.

Also related to the small size of the light-particle interaction region in a typical flow cytometer, is the fact that some lasers display intrinsic high-frequency intensity fluctuations referred to as Relative Intensity Noise (RIN). During the short transit time of the particle in the light beam, a short pulse of fluorescing and scattered light is generated. If the laser intensity changes significantly during this transit time, the amplitude of the generated pulse will also fluctuate in a manner that is not correlated to the properties of the particle but as a consequence of the temporal instability of the laser source and hence create a hard-to-interpret measurement artifact. Therefore, it is important to use a stable laser with a low RIN at the frequency corresponding to the reciprocal duration of the transit time, typically ranging from 1 MHz to 10 MHz. Similar considerations must be applied to the spatial uniformity of the laser beam in the plane of the transit region, because a spatially non-uniform beam (especially when the spatial non-uniformity is time-varying because of vibrations or thermal effects) will produce non-uniform excitation during the transit and hence result in non-uniform amplitude in the pulsed fluorescent or scattering signals generated by the interaction between the laser light and the transiting particle. This in turn leads to the same equivocal interpretation of the signals and of its origin described above. Once again, this imposes additional constraints on the quality of the laser spatial and temporal properties and complexity of the signal processing used to mitigate these artifacts.

Therefore, a need exists for an improved and simplified beam delivery system to mitigate the problems of measurement and overall bulkiness and cost of the apparatus.

SUMMARY

There is provided an apparatus for fluid analysis which considerably simplify the beam delivery subsystems of the prior art by replacing the complex geometry of the capillaries for the optimized collection of scattered light by an optical fiber serving as the interaction flow cell while providing the added benefits of intrinsic beam shaping, beam delivery and simplified fluidics. This combination of attributes allows for the miniaturization of the bulky beam delivery and sheath flow subsystems used in standard flow cytometers.

The provided flow cytometry platform enables the detection of microscopic particles and cells for clinical diagnostics, environmental, and quality control markets, to just name a few.

There is provided an apparatus and method for analyzing a fluid with particle analytes, where the fluid is fed through a passageway within an optical fiber and excitation light is guided by the optical fiber across the passageway and intersects the fluid therein. The optical core is made multimode and is adapted to shape the excitation light with a uniform spatial illumination over a cross-section of the optical core. The passageway is configured relative to the optical core such that the particle analytes are all exposed to substantially equal excitation light while circulating in the passageway.

In accordance with a first broad aspect, there is provided an apparatus for use in analyzing a fluid with particle analytes comprising: a light source unit for providing an excitation light; an interrogation optical fiber optically connected to said light source unit for receiving said excitation light and comprising: an optical core extending along a longitudinal axis of said interrogation optical fiber for guiding said excitation light, said optical core being multimode and being adapted to shape said excitation light with a substantially uniform spatial illumination over a cross-section of said optical core; and a passageway extending throughout said interrogation optical fiber in a transverse direction relative to said longitudinal axis of said interrogation optical fiber such that said passageway intersects said optical core, said passageway for circulating said fluid across said interrogation optical fiber and being shaped such that circulating particle analytes cross said excitation light as said excitation light propagates through said passageway, an intersection of said fluid in said passageway and said excitation light defining an interaction volume wherein a result of an interaction of said excitation light and said particle analytes is representative of a parameter to be analyzed, said passageway being configured relative to said optical core such that said particle analytes are exposed to said excitation light for a generally same duration of time while circulating in said passageway; a channeling unit connected to said passageway to circulate said fluid and its particle analytes through said passageway; and a light detection unit for detecting said result of said interaction of said excitation light with said particle analytes.

In accordance with a further aspect, said light source unit comprises a light emitting diode.

In accordance with a further aspect, said light detection unit is connected to an output of said interrogation optical fiber for detecting a change in said excitation light resulting from said interaction.

In accordance with a further aspect, the apparatus further comprises a light collection unit located along said interrogation optical fiber in the vicinity of said passageway and in a transverse orientation relative to said longitudinal axis of said interrogation optical fiber, for collecting light resulting from said interaction of said excitation light with said particle analytes of said fluid.

In accordance with a further aspect, said optical core has a substantially rectangular cross-section.

In accordance with a further aspect, said passageway has a substantially quadrilateral frustum shape.

In accordance with a further aspect, a numerical aperture of said interrogation optical fiber and a central wavelength of said excitation light are such that a speckle appearing in said excitation light has a size that is smaller than a size of said particle analytes.

In accordance with a further aspect, a number of transversal modes of propagation of said excitation light in said interrogation optical fiber is at least 1000.

In accordance with a further aspect, said passageway comprises a capillary extending through said passageway and across said interrogation optical fiber and adapted to channel said fluid and said particle analytes through said passageway.

In accordance with a further aspect, an inside surface and an outside surface of said capillary have a substantially rectangular cross-section.

In accordance with a further aspect, the apparatus further comprises a band-pass filtering module located between said light source unit and said passageway.

In accordance with a further aspect, said interrogation optical fiber comprises a first fiber section located between said input and said passageway and a second fiber section located on an opposite side of said passageway relative to said first fiber section, wherein said first and said second fiber section are dissimilar in at least one of a geometry and an optical property.

In accordance with a further aspect, said first fiber section and said second fiber section are joined on a subregion of their cross-section excluding said passageway.

In accordance with a further aspect, said first fiber section and said second fiber section are partly fusion-spliced together so as to form said passageway in between.

In accordance with a further aspect, said passageway is a hole defined in said interrogation optical fiber.

In accordance with a further aspect, said hole is bored in said interrogation optical fiber using at least one of contact micro-machining, non-contact micro-machining and chemical etching.

In accordance with a further aspect, the apparatus further comprises a mirror located at an output of said interrogation optical fiber for reflecting said excitation light back into said interrogation optical fiber.

In accordance with a second broad aspect, there is provided an apparatus for use in analyzing a fluid with particle analytes, the apparatus comprising: an interrogation optical fiber having an input optically connectable to a light source for receiving an excitation light, a core extending along a longitudinal axis of said interrogation optical fiber for guiding said excitation light, and a hole extending throughout said interrogation optical fiber in a transverse direction relative to said longitudinal axis of said interrogation optical fiber and traversing said interrogation optical fiber directly through said core for circulating said fluid such that circulating particle analytes cross said excitation light as said excitation light propagates through said hole; and a light collection unit located along said interrogation optical fiber in the vicinity of said hole for collecting light resulting from said interaction of said excitation light with said particle analytes of said fluid.

In accordance with a further aspect, said interrogation optical fiber has a collection surface on its outer cladding surface and in the vicinity of said hole which is one of a flat surface and a surface engraved in said outer cladding surface and which is adapted to collect said light resulting from said interaction of said excitation light with said particle analytes, said light collection unit being disposed adjacent to said collection surface.

In accordance with a further aspect, said collection surface is a surface engraved in said outer cladding surface in the shape of one of a spherical lens, an aspherical lens and a conical lens.

In accordance with a further aspect, said light collection unit comprises at least one collection optical fiber.

In accordance with a further aspect, the apparatus further comprises a mirror located at an output of said interrogation optical fiber for reflecting said excitation light back into said interrogation optical fiber.

In accordance with a further aspect, the apparatus further comprises a capillary extending along said hole and across said interrogation optical fiber and adapted to channel said fluid and said particle analytes through said hole.

In accordance with a further aspect, said capillary has a substantially rectangular cross-section.

In accordance with a further aspect, said core of said interrogation optical fiber has a substantially rectangular cross-section.

In accordance with a further aspect, said hole has a substantially rectangular shape.

In accordance with a further aspect, the apparatus further comprises a band-pass filter positioned between said input of said interrogation optical fiber and said hole.

In accordance with a further aspect, said interrogation optical fiber has an input optically connectable to a light source unit and wherein said light source unit is a light emitting diode.

In accordance with a further aspect, a numerical aperture of said interrogation optical fiber and a central wavelength of said excitation light are such that a speckle appearing in said excitation light has a size that is substantially smaller than a size of said particle analytes.

In accordance with a third broad aspect, there is provided a method for analyzing a fluid with particle analytes, the method comprising: producing a substantially uniform spatial illumination over a cross-section of an optical core of a multimode interrogation optical fiber by injecting an excitation light in said interrogation optical fiber for propagation in said optical core; exposing each of said particle analytes of said fluid to substantially equal excitation light by channeling said fluid through a passageway extending throughout said interrogation optical fiber and intersecting said optical core of said interrogation optical fiber such that said fluid circulates across said optical core; and detecting a result of an interaction of said excitation light and said particle analytes to determine said parameter to be analyzed.

In accordance with a further aspect, said detecting comprises detecting said result at an output of said interrogation optical fiber.

In accordance with a further aspect, said detecting comprises collecting said result on a side of said interrogation optical fiber in the vicinity of said passageway and in a transversal direction relative to the interrogation optical fiber.

In accordance with a further aspect, the method further comprises selecting a numerical aperture of said interrogation optical fiber and a central wavelength of said excitation light such that a speckle appearing in said excitation light has a size that is smaller that a size of said particle analytes.

In accordance with a further aspect, said producing comprises propagating at least 1000 transversal modes of propagation of said excitation light in said optical core of said interrogation optical fiber.

In accordance with a fourth broad aspect, there is provided a compact and sheathless particle-based biodetection system for one of field-based, remote, and portable applications involving at least one of monitoring, diagnosing, testing and point-of-care testing via cell counting using at least one of fluorescence, scattering and imaging modalities.

In accordance with a further aspect, said particle is a cell-sized fluorescent particle.

Complex excitation and collection optics of prior art cytometers are replaced by fiber optics such that the optical alignment is all made in the fabrication process. Further, sheath fluid which increases assay costs and generation of biohazard materials is no longer necessary. This allows the apparatus to be used for field and autonomous remote operations.

The apparatus is used for studying small bodies in a fluid medium. In one embodiment, the passageway is a hole through the core of the optical fiber in a substantially transversal orientation. The hole can have or be devoid of a symmetry axis, e.g. the hole may be a non-symmetrical taper, a taper with a symmetry axis making an angle with a direction transverse to the optical fiber, a non-tapered passageway of a given cross-sectional shape, etc. . . . At least one of the small bodies is thus analyzed by assessing the detected exiting light intensity.

BRIEF DESCRIPTION OF THE DRAWINGS

It will be noted that throughout the appended drawings, like features are identified by like reference numerals.

DETAILED DESCRIPTION

Figure 1:
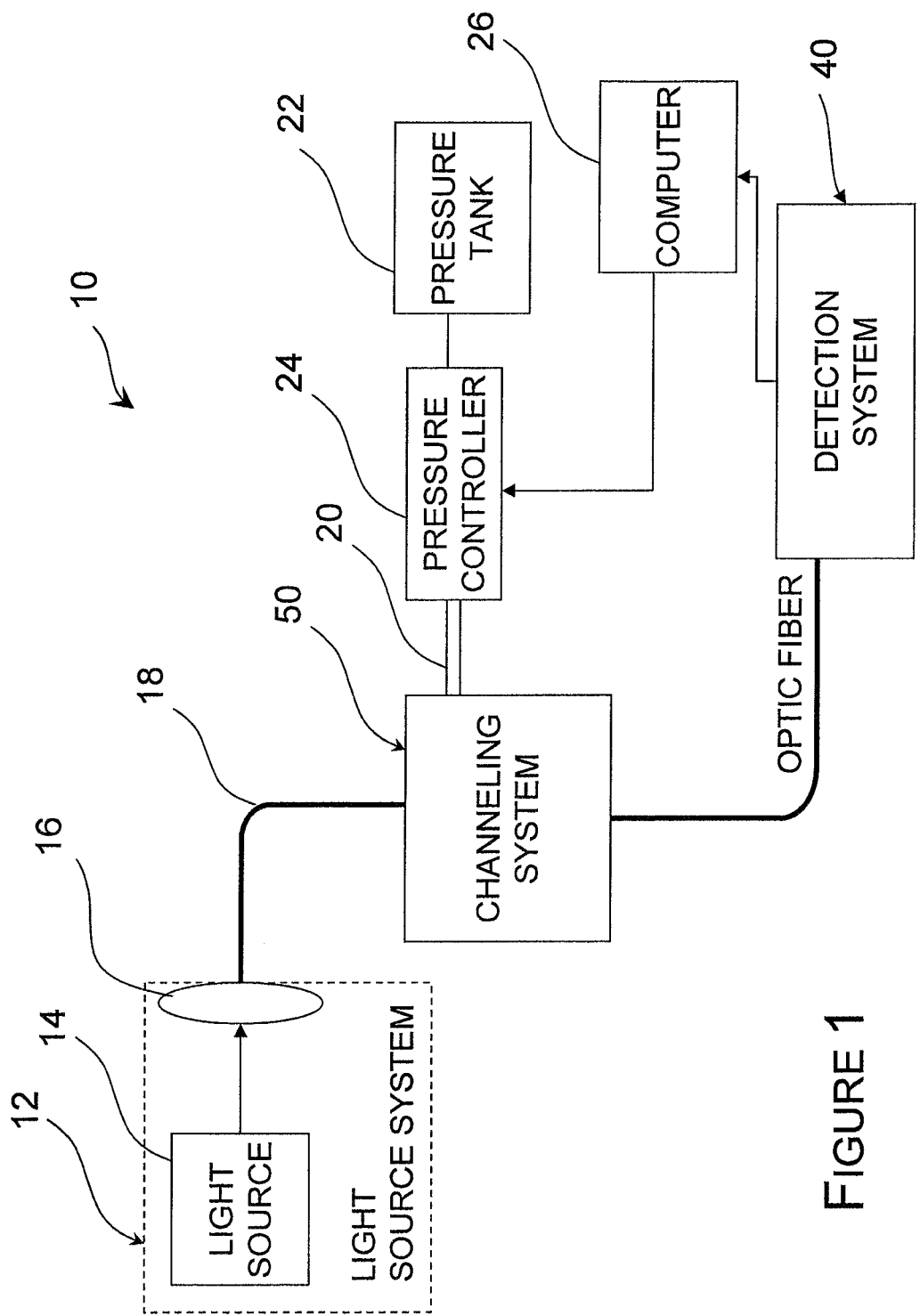
FIG. 1 is a block diagram of the main components of a system for studying a fluid, in accordance with one embodiment of the present invention.
Figure 2:
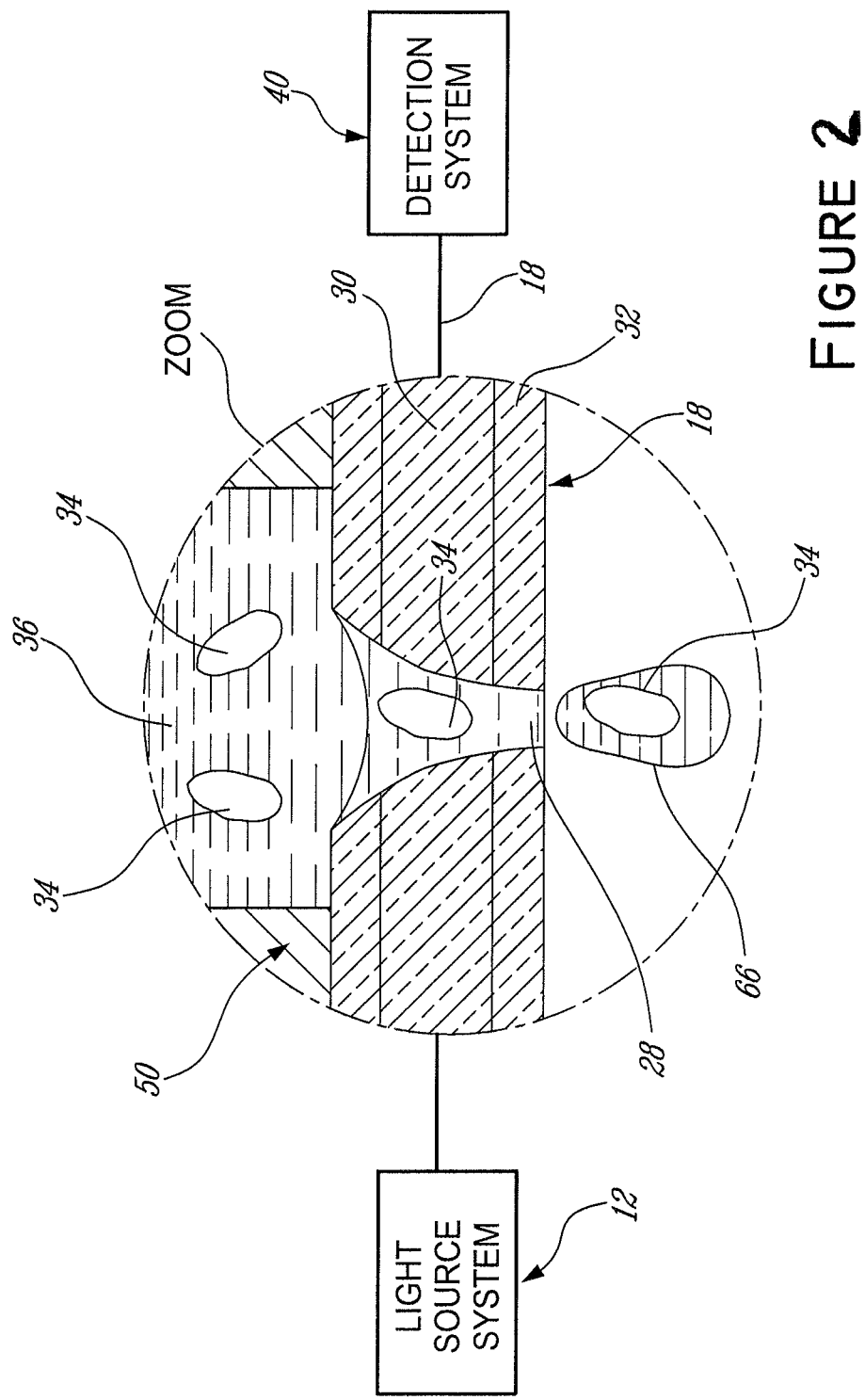
FIG. 2 is a schematic view, partly enlarged, of the intersecting action of a light beam and a small body within the passageway created in the optical fiber of the system of FIG. 1.

FIG. 1 schematically illustrates the main components of a system 10 in accordance with one embodiment. A light source system 12, preferably including a light source 14 and an injection lens 16, injects excitation light in an interrogation optical fiber 18. The excitation light is light used to interact with particle analytes transiting in the optical fiber 18 which has a passageway defined within it, such as a transversal hole 28 as depicted in FIG. 2. Said excitation light can be used to measure the scattering properties of the particles or stimulate fluorescence of the particles or both. The excitation light propagates in the core 30 of the optical fiber 18 and across the transversal hole 28. It is to be noted that FIG. 2 is a schematic view and is therefore not a true representation of the appearance of the transversal hole 28 and the core 30 of the optical fiber.

A channeling system 50 channels a fluid through the passageway, where the fluid interacts with the propagating excitation light. In this embodiment, the flow rate of the fluid through the passageway in the optical fiber 18 is controlled by varying its pressure, and thus a pressure inlet 20 is provided to connect the channeling system 50 to a pressure tank 22 via a pressure controller 24, which is preferably controlled by a computer 26. Information about the fluid and its reaction to being traversed by such excitation light is extracted by analyzing the intensity of light exiting the optical fiber 18. A detection system 40 is used to monitor the variation of exiting light intensity with time and to monitor the intensity of light at precise wavelengths, from which the desired information is extracted. It is noted that the monitored exiting light may exit an output of the optical fiber 18 or, alternately or concurrently, may be light exiting from a side of the optical fiber 18 and collected using a light collection unit as will be discussed hereinafter. The detection system 40 is typically also connected to a computer 26. The fluid includes particle analytes also referred to herein as small bodies, and the system is used to study the particle analytes within the fluid, but the system can also be used to study a homogeneous solution. In the one embodiment, the small bodies are bacteria, cells or beads, either enhanced or not with fluorophores and analyte-specific reagents, and the fluid medium is chosen as to increase or decrease survivability of the living small bodies depending on the intended purpose.

The intersection of the excitation light and small bodies in the system 10 is schematically illustrated in FIG. 2, where the portion of the optical fiber 18 having the transversal hole 28 is schematically enlarged. The small bodies 34 in the fluid medium 36 are channeled through the hole 28, and the excitation light propagates in the core 30 of the optical fiber 18. The hole 28 runs through the core 30 and the cladding 32 of the optical fiber 18 in a transversal direction. Preferably, the hole 28 has a slightly frusto-conical shape inclined by of a few degrees relatively to a perpendicular axis to the optical fiber 18 (exaggerated on the Figures). This shape results from the drilling fabrication process and is not necessary; it has a negligible effect on light attenuation. Other fabrication processes such as laser micro-machining or chemical etching allow other shapes and alignment to be implemented. When a small body 34 passes in the hole 28, its trajectory intersects the light beam from the light source system 12 which travels within the core 30 of the optical fiber 18 and across the hole. The light intensity exiting the optical fiber 18 is thus modulated due to the interaction of the light with the content of the hole 28. Those modulations are detected with the detection system 40 which allows extracting information about the small bodies 34. In certain applications, fluorescence light is emitted by the small bodies 34 in response to stimulation at the wavelength of the guided light propagating in the optical fiber 18. The fluorescence is either partly guided in the optical fiber 18 or escape from its side and can be detected by the detection system 40 positioned accordingly.

Figure 3:
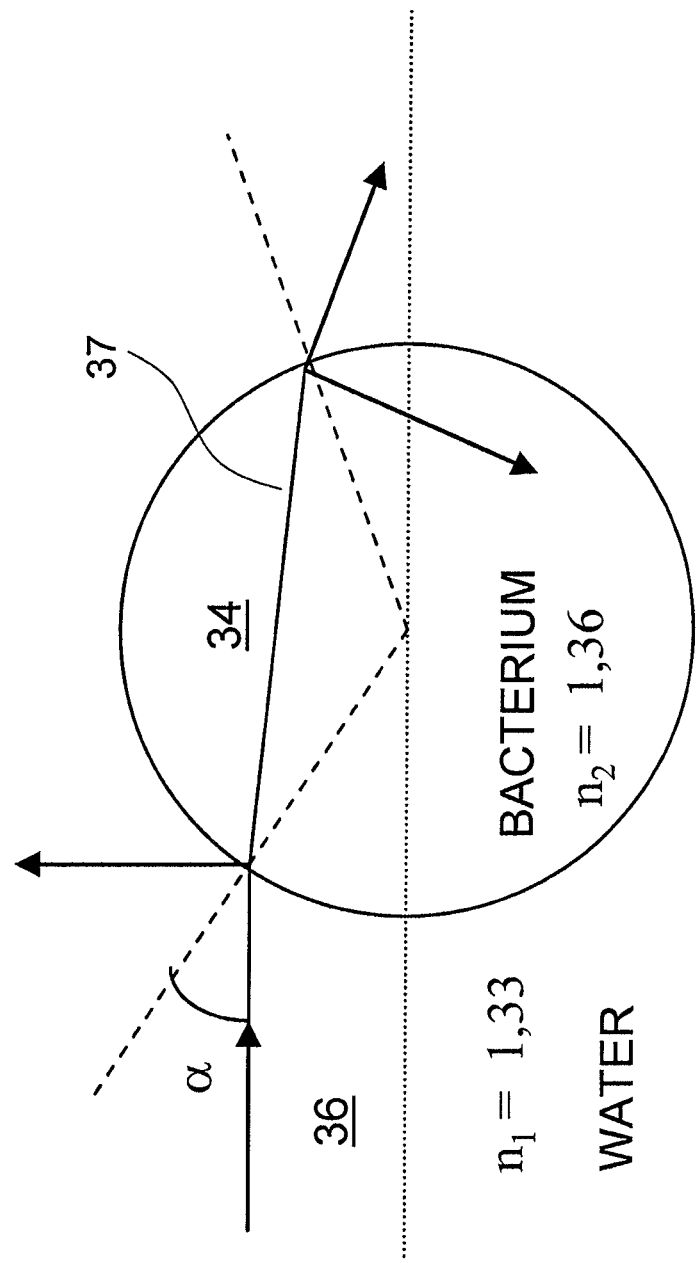
FIG. 3 is a schematic view, enlarged, of the interaction of a ray of light intersecting a small body and being attenuated in the system of FIG. 1.

In one embodiment, the apparatus is used to analyze bacteria 34 in a fluid medium 36. The presence or absence of a bacterium 34 within the hole 28 affects the output and nature of the light from the optical fiber 18. The interaction between a small body and a ray of light is schematically depicted in FIG. 3. Experimental results from a research team of the Memorial University of Newfoundland show that the refractive index of bacteria is from 3% to 6% higher than the refractive index of water. Hence, when a ray of light 37 crosses a bacterium 34 in the hole, it crosses two surfaces of the bacterium, an entrance and an exit. Due to the difference in the refractive index between the two substances, refraction occurs if the angle of incidence is not of 0 degree, and the direction of the ray is varied. This is referred to as light scattering by those skilled in the art. Depending on the relative size of the particle to the wavelength of the excitation light, two regimen are described theoretically; Rayleigh scattering when the wavelength is large compared to the dimension of the particle and Mie scattering when the wavelength is of the order or smaller than the size of the particle. Further, scattered light is emitted in all directions and is generally referred to side scattering for large angle deviations from the direction of the incident light and forward scattering for small angle. The consequence of this is that the intensity of light that successfully crosses the hole is attenuated when a small body 34 is present. Also, the attenuation is larger when the small bodies or particle analyte are labeled with fluorophores (e.g. dyes), because light is absorbed by these dyes and leads to fluorescence at different wavelengths than the excitation light. This will be discussed further down.

Thus, the output intensity of light exiting the optical fiber 18 from its output, i.e. forward scattering and fluorescence, and its side, i.e. side scattering and fluorescence, carries information enabling to detect the presence or absence of a bacterium 34 in the hole 28. By extending this experimentation over time, with the fluid medium 36 flowing within the hole 28 at a controlled flow rate, it is possible to count the number of bacteria 34 which have passed through the hole. This allows one to study the quantity or density of bacteria 34 in the fluid medium 36. Further, the size of the individual bacterium 34 intersecting the beam will affect the intensity attenuation in the beam. Therefore, with sufficiently precise instruments in the detection system 40, and appropriate algorithms which will be discussed further down, it is possible to measure the attenuation of the light and to evaluate the size of the bacteria 34 in the fluid medium 36. Consequently, when it is desired to obtain information concerning individual bacterium 34, ideal results are obtained when the region of the hole 28 where the bacteria and the light intersect is not much larger than the size of a bacterium 34. The bacteria 34 are then forced to pass across the light beam one by one.

Ideally, a fluid medium having the same index of refraction than the core of the optical fiber is used to maximize the transmission of light. However, the variation of the light intensity resulting from the passage of a bacteria can be amplified, and the absolute value of the intensity is not therefore of utter importance. If fluorescence light intensity is detected, as will be discussed further down, the quantity of light detected diminishes as a function of the difference between the indices of refraction. This diminution relatively to the ideal configuration is generally below 3%, and is thus of little relative importance.

Depending on the application, the size of the hole can be varied between a few to several tens of microns in diameter to accommodate the study of different sizes of small bodies. Typically, in the case of bacteria, the hole has a diameter between 25 and 50 μm. As it is shown in FIG. 2, the hole 28 is generally defined in a transversal orientation relatively to the axis of the optical fiber 18, in order to maximize light propagation across it. The hole 28 is preferably created by laser micro-machining, although other techniques may alternatively be used.

The system of FIGS. 1 and 2 is adaptable to a variety of alternative applications. Alternative embodiments to the apparatus include using a single mode optical fiber, using optical fibers with a core of different size, using an optical fiber with a different outer diameter, and using a transversal hole of different size or shape. As it is known in the art, the world of optical fibers is evolving rapidly and new types of fibers such as photonic crystal fibers have emerged which do not have the same type of cores and claddings as traditional fibers. Such unconventional fibers may be used if they are determined to be suitable for specific applications. Henceforth, the definition of the term core herewithin is not to be understood as limiting to the traditional meaning of cores, but rather to the region of the fiber wherein the light is guided. Furthermore, optical fibers with core diameters ranging from a few microns to over 200 μm are routinely available. The size of the hole may thus be varied between a few to several hundred microns in diameter to accommodate the study of different sizes of small bodies by selecting an appropriate optical fiber. The alternatives used will typically be selected to enhance transmission characteristics and to adapt the apparatus either to different sizes of small bodies 34 or to different information to be analyzed, the exact choice is thus left entirely to those skilled in the art realizing specific embodiments of the invention subsequently to routine experimentation.

Figure 4A:
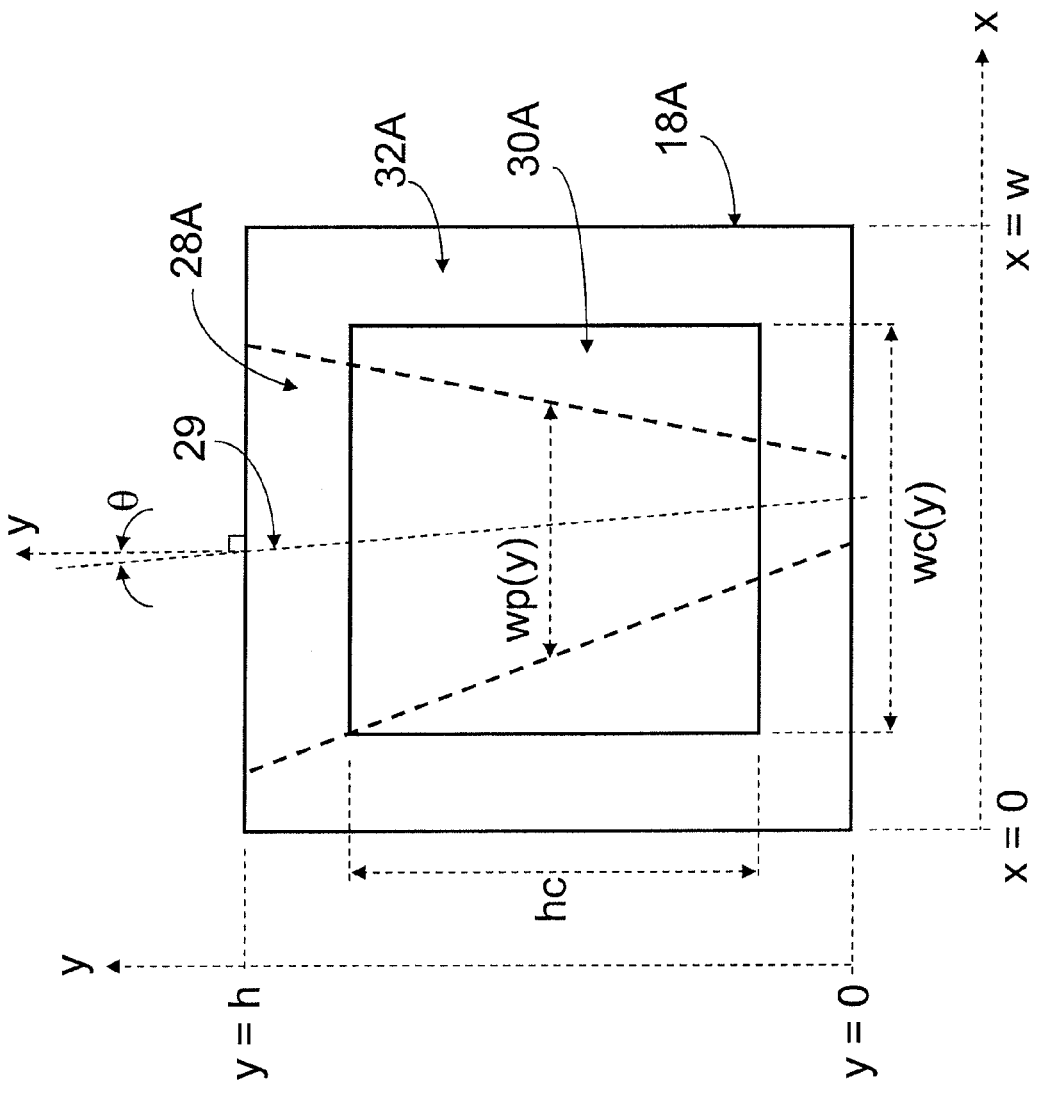
FIG. 4A is a schematic cross-sectional view of an interrogation optical fiber with a square optical core and a tapered transversal hole for use in system of FIG. 1.

Optimization of the fiber physical and geometrical parameters to improve the beam uniformity of the excitation light propagating from the light source 14 can result in having a core 30 of different shape than illustrated in FIG. 2. The same considerations apply to the transversal hole 28A. FIG. 4A illustrates a generic embodiment of an interrogation fiber 18A with a transversal hole 28A and defining an interaction region of the excitation light with the fluid and its particle analytes. The width w and the height h of the optical fiber 18A are defined in a x-y Cartesian coordinates system having its origin in the lower left of FIG. 4A. With respect to this coordinates system, a cross-sectional area of the core 30A has a width $wc(y)$ and a height $hc(x)$, a cross-sectional area of the cladding 32A has a width $w(y)$ and a height $h(x)$, and a cross-sectional area of the transversal hole 28A has a width $wp(y)$ and a height equal to $h(x)$ by definition since the hole is completely traversing the optical fiber 18A. Further, an axis of symmetry 29 can be defined as the general direction of the flow of the particles passing through the transversal hole 28A, this axis making an angle equal to θ with respect to y in the defined coordinates system.

In order to provide an optical fiber-based delivery system this is both cost-effective and performing, an important condition applying to cytometry is that every single particle analyte transiting through the interaction region, irrespective of its specific path, is excited uniformly both spatially and temporally, that is by being exposed to a uniform light field for the same duration of time. The embodiments described herein realize this condition in a simple, compact and cost-effective way.

In one embodiment, it is important to note that two conditions should be respected with regard to wp and wc in order for all the particle analytes transiting through the hole 28A to be illuminated for a substantially equal amount of time irrespective of their specific position in the flow. The first condition requires that $wc(y)$ be equal or larger than $wp(y)$ for the domain of values of y where $wc(y)$ is greater than 0, that is throughout the height of the core. The second condition requires the cross sectional area of the hole 28A to be completely overlapped by the cross-sectional area of the core 30A with respect to their width position along the axis x.

Figure 4B:
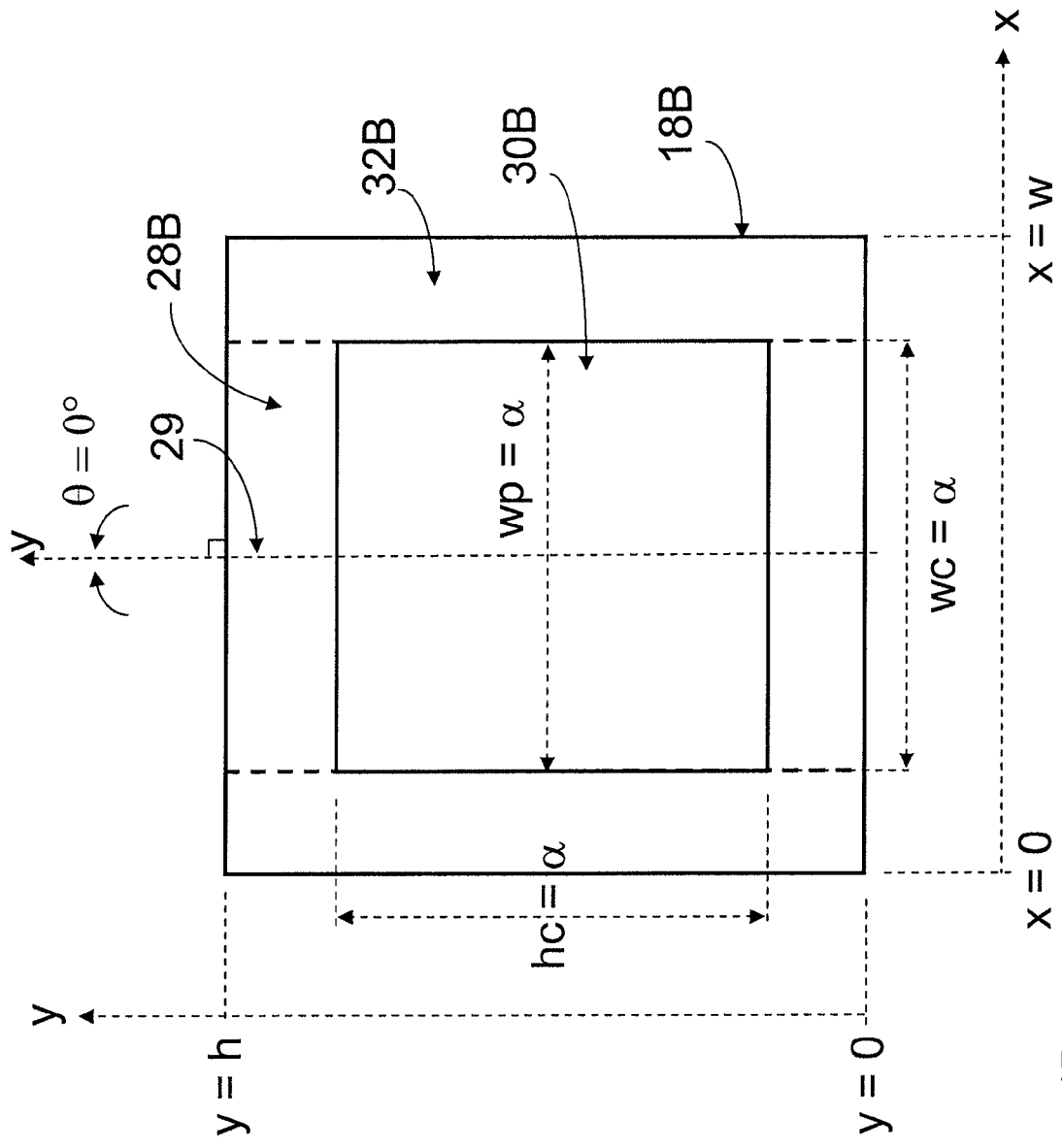
FIG. 4B is a schematic cross-sectional view of an interrogation optical fiber with a square optical core and a rectangular transversal hole for use in system of FIG. 1.
Figure 4C:
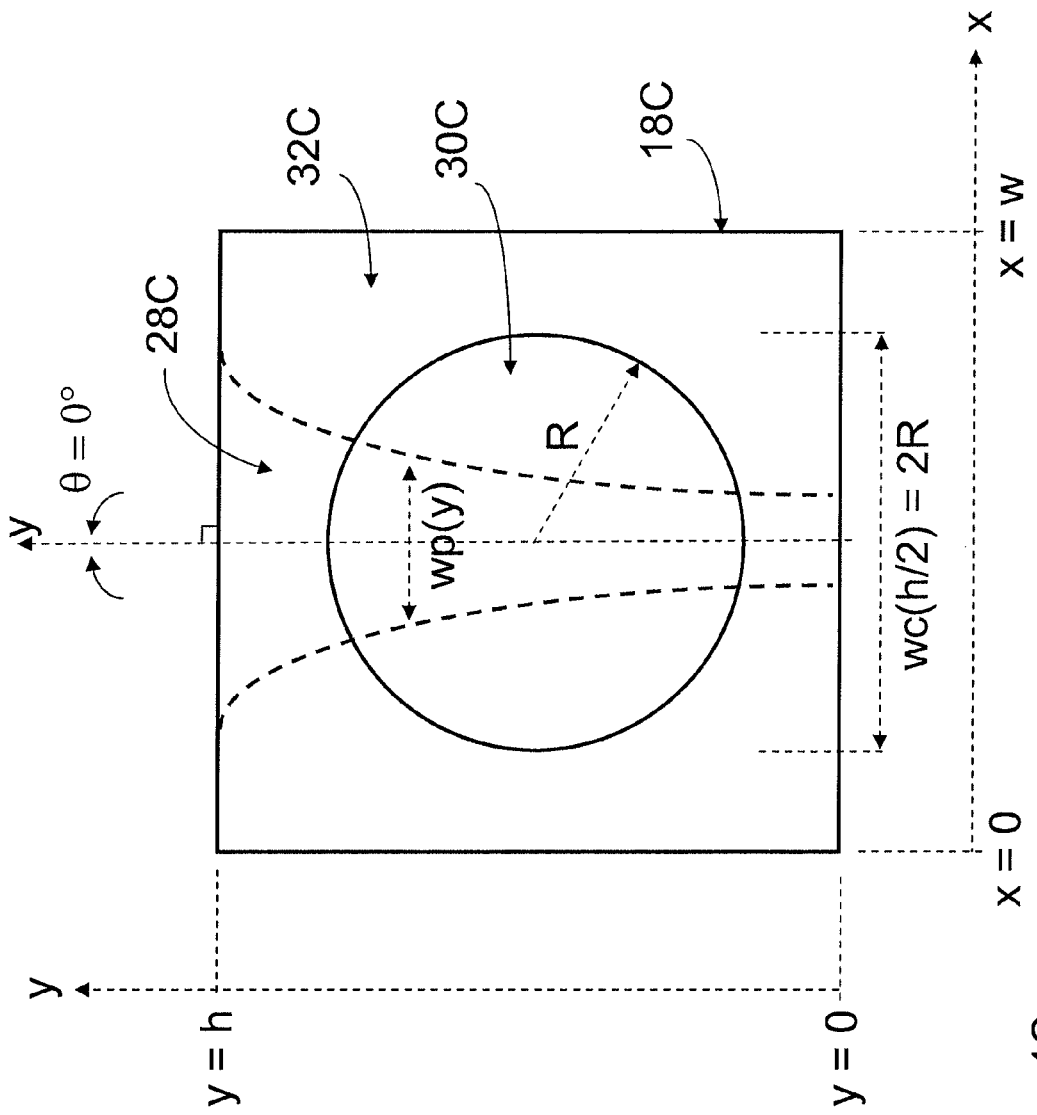
FIG. 4C is a schematic cross-sectional view of an interrogation optical fiber with a circular optical core and a funnel-shaped transversal hole for use in system of FIG. 1.

It is important to recognize that $wc(y)$ and $wp(y)$ can be generic functions of height y. For example, $wc(y)$ and $wp(y)$ can be linear, parabolic, hyperbolic functions or elliptic relations of y. FIG. 4B illustrates an example of an interrogation optical fiber 18B with $wc(y)$ and $wp(y)$ being linear functions and where wc and wp are equal to a constant α throughout the height of the core 30B. In the specific case where hc=α and θ=0, this would represent a hole 28B with a rectangular cross-section and a core 30B having a square cross-section as presented in FIG. 4B. In another example of an interrogation optical fiber 18C illustrated in FIG. 4C, a relation would be $(x-w/2)^2+(y-h/2)^2=(wc/2)^2$ to represent a circular core 30C of radius we/2 concentric with the cladding 32C and centered at h/2 and w/2. As long as the two conditions discussed above are respected (which would be approximately the case for $wp(y) \ll R$ and an axis 29 positioned at x=w/2 as in FIG. 4C, particles transiting through the hole 28C would be illuminated for substantially the same duration of time irrespective of their specific position in the flow. Optimizing the relative shape and overlap of the core and the hole cross-sections in a practical context could be found by one skilled in the.

In one embodiment, the optical fiber 18 is designed and optimized to simplify the light delivery system to the region of interaction with the small bodies passing through the transverse hole 28. The use of an optical fiber from the laser to the interaction region avoids the use of bulky optical elements to shape the beam and homogenize its spatial distribution. In classical cytometry, expensive lasers having excellent beam quality are used to create very small focused spot on the individual particles crossing the region of interaction. The use of bulky optical elements such as lenses and spatial filters to achieve such tight spot size complicates greatly the alignment of the beam delivery system and hence necessitate highly-trained personnel. This also makes for systems sensitive to vibrations and shock-induced misalignment. Unfortunately, the alternative of using an optical fiber as a beam delivery system in classical cytometry is not as appealing as it may seem. The tight focusing in the region of light-particle interaction would require injecting and propagating the laser beam in a small-core single-mode fiber, notoriously prone to be even more sensitive to misalignment than bulk optics. This is the reason why it is avoided by classical cytometer manufacturers.

In one embodiment, the interaction region defined by the transversal hole 28 is from 10 to 100 times larger than in classical cytometry and thus would allow the use of larger-core multimode optical fiber to deliver the laser light to the interaction region, these fibers allowing better injection efficiency than single-mode fibers. However, standard multimode fibers are also known to produce large size speckle (i.e. spatial granularity of the intensity) and non-uniform time-varying (because of vibrations and small thermal fluctuations in the environment of the fiber) illumination at their output because of intermodal coupling of a limited and changing number N of stimulated transverse modes of propagations resulting from the sensitivity of the light injection conditions at their input (e.g. radial position of the injected light, its spatial profile, its angle with respect to the input plane, etc. . . . ). It An optimized design of fiber produces excellent spatial beam uniformity in the core 30 and therefore at the output of the beam delivery system by favoring the coupling of a large number N of transversal modes, typically larger than 1000, while maintaining the simplicity and excellent radiometric stability characteristics of injection in multimode fibers.

In addition to the geometrical considerations described above regarding the relative size and overlap of the cross-sections of the optical fiber core 30 and the hole 28, an optimized optical fiber design is such that any two particles successively passing through the interaction region is submitted to the same intensity of excitation light over a similar period of transit time irrespective of the specific path they follow within the interaction region. Accordingly, the light intensity in a transversal plane of the optical fiber core 30 should be spatially uniform. The theory of speckle defining the spatial granularity of the intensity fluctuations across the transversal dimensions of the core, teaches that the size of speckle is proportional to $\lambda/2NA$ where NA is the numerical aperture of the fiber and $\lambda$ the wavelength of the light propagated in the core. Reducing the speckle size to below the typical size of the particle to be analyzed (typically smaller than 1 µm) requires as high a numerical aperture, a feature desirable also to increase the efficiency of light injection at the input of the optical fiber. For example, with an optical fiber having a large numerical aperture of approximately 0.4, a square-shaped core having sides of 100 µm and propagating excitation light at $\lambda=500$ nm, particles passing through the interaction region are submitted to light spatially fluctuating over more than 150 periods of speckle, a value providing a significant averaging statistics. In any case, the size of speckle should be smaller than the size of the particle analytes. Such specialty optical fibers are available from INO (Institut National d'Optique), Québec, Canada. The cross-sectional area of the core will typically be at least $10^2$ µm$^2$ and up to $10^6$ µm$^2$ for analysis of particle analytes typically larger than 0.5 µm.

In addition to the design described above to provide uniform illumination of the small bodies passing through the hole 28, the interrogation optical fiber has numerous other advantages. First, with suitable choices of fiber geometry and optical properties, systems extremely tolerant to vibrations, shocks and thermally-induced misalignment can be implemented. Second, the outer surface of the fiber can be shaped along the longitudinal direction as to help in optimizing collection of side scattered of fluorescence light emitted in the interaction region. For example, a square-shaped outer cladding surface can provide flat collection surfaces mitigating lensing effects that would be induced by using a standard optical fiber of cylindrical shape. Many variations can be implemented and optimizing the shape of the outer surface of the outer cladding of the optical fiber in a practical context may be found by one skilled in the art. For example, the shaped outer surface may have properties of one or multiple spherical, aspherical, conical or cylindrical lens. Thirdly, forward scattering light generated in the light-particle interaction region can be captured by the interrogation optical fiber and guided towards its output where a detector is placed and adequately masked to remove the excitation light guided in the core. In that regard, a double-clad fiber as discussed in further details below helps in guiding with minimal losses the forward scattering light collected. One advantage of fiber collection of forward scattering light over classical cytometry set-up is the capability to bring the collected light to a detector that does not have to be collinearly positioned with the excitation light. This allows for a more compact folded system.

Instead of being provided as a transversal hole in the fiber, the passageway for the fluid within the optical fiber can be provided differently, as will appear to those skilled in the art. For example, the optical fiber could be cut in two optical fiber sections, and the two sections can be held spaced apart at a distance allowing light from one optical fiber section to at least partly travel across the passageway thereby defined, and into the other optical fiber section to continue to be guided therein. In order to facilitate this type of passageway, the two optical fiber section can be partly fused together in order to only create a tubular or differently-shaped channel within the fiber where the fluid will be able to travel.

It will be readily understood that instead of cutting one fiber into two pieces, two fibers, with similar or different geometries and/or optical properties, could be used and aligned to create the passageway. Other ways of creating the passageway could also be found by one skilled in the art and are intended to be covered by the present invention. For practical reasons, the transversal hole 28 embodiment for the passageway is preferred. Therefore, to simplify the text, the passageway is be referred to as a transversal hole created in the fiber hereinafter, independently of its specific construction, shape or orientation in relation to the optical fiber.

Figure 5:
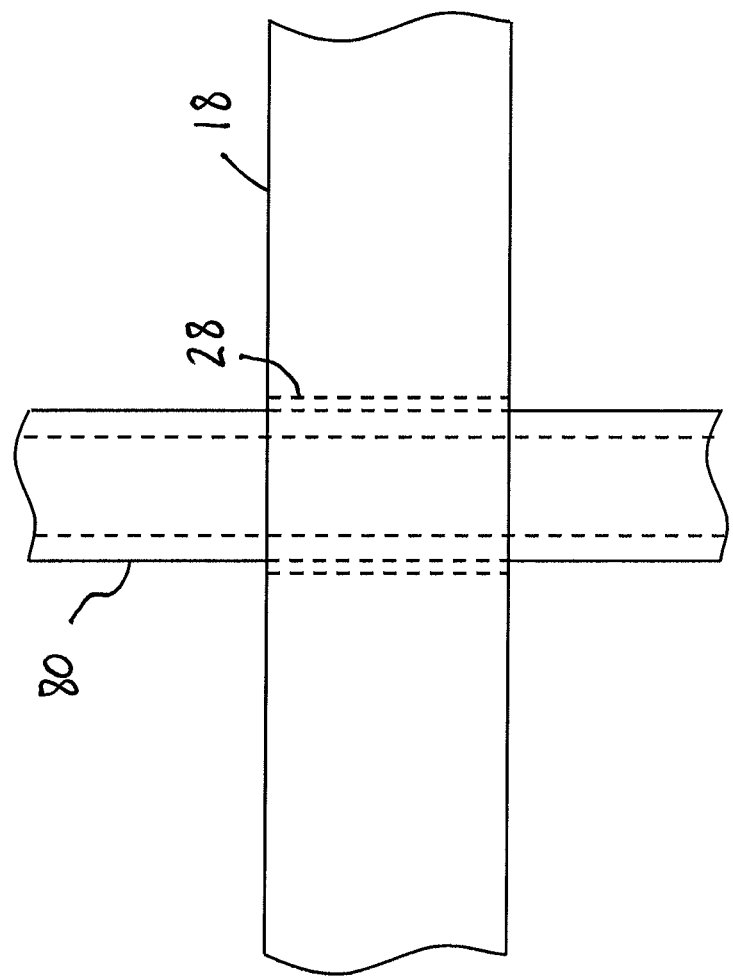
FIG. 5 is a schematic side elevation view, fragmented, of an example fiber optic flow cell apparatus to be used in the system of FIG. 1, where the interrogation optical fiber has a transversal hole with a transparent channel support inserted therein.

In one embodiment illustrated in FIG. 5, a transparent channel support 80, such as a capillary, a hollow tube or a hollow optical fiber of various cross-sections, allowing light to propagate therethrough is inserted within the passageway to facilitate fusing of the two cut ends of the fiber 18 while ensuring a specific shape and size for the hole 28. The transparent channel support 80 is made of a material substantially transparent to the excitation light propagating in the interrogation fiber 18 such that the light propagates through the transparent channel support 80. The transparent channel support 80 is used to bring the sample into the hole 28 of the interrogation fiber 18, thereby reducing the complexity of the opto-fluidic packaging. In one embodiment, the capillary, hollow tube or hollow optical fiber has elliptical inner and outer cross-sections. In another embodiment, it has rectangular inner and outer cross-sections.

In one embodiment, the transparent channel support 80 is a borosilicate square capillary of 115/60 µm (VitroCom™, NJ) inserted into a square hole. An optical epoxy resin with low auto-fluorescence is inserted between the walls of the squared hole and the capillary. The assembly is mounted on a proto-type aluminum block to assure its robustness. It is noted that the transparent channel support 80 may also be made of other materials such as fused silica or fused quartz, for example.

It should be understood that the fiber optic flow cell may comprise no capillary. In this case, the fluid to be analyzed is brought to the excitation fiber via an inlet and flows directly in the hole.

Figure 6:
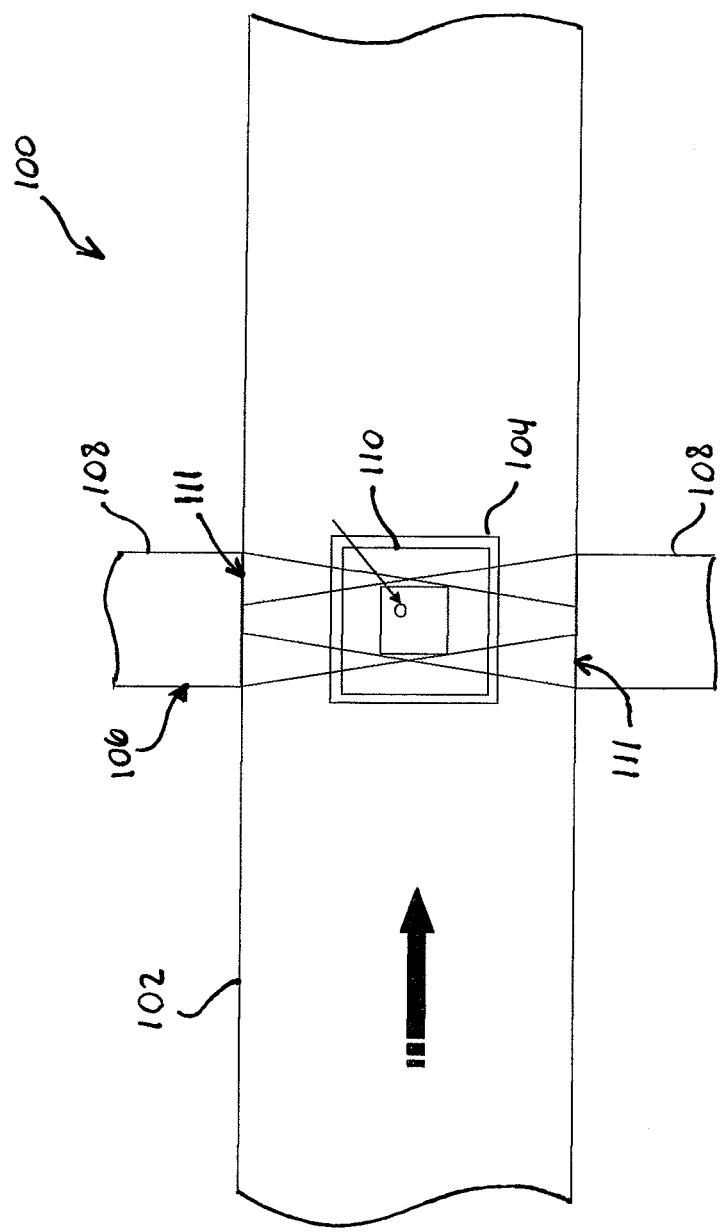
FIG. 6 is a schematic top plan view, fragmented, of an example fiber optic flow cell apparatus to be used in the system of FIG. 1, wherein a light collection unit is disposed in a vicinity of the transversal hole.

FIG. 6 schematically illustrates another embodiment of a fiber optic flow cell apparatus 100 which can be used as a fiber optic flow cytometer. In this case, the flow cytometer is referred to as a side light collection flow cytometer since light is collected on the side of the interrogation fiber 102 in the vicinity of the hole where travels the fluid to be analyzed. The fiber optic flow cell 100 comprises an interrogation fiber 102 in which a hole 104 has been created transversally to the light propagation axis and a light collection unit 106 located along the interrogation fiber 102 in the vicinity of the hole 104 and comprising at least one and in this case two collection fibers 108. A fluid to be analyzed propagates through the hole 104 and interacts with the light propagating into the interrogation fiber 102. In this illustrated case, a capillary 110 is inserted in the hole 104 and the fluid travels in the capillary 110. At least a portion of light interacting with the fluid to be analyzed is scattered and a portion of the scattered light is no more guided into the core of the interrogation fiber 102 and exits to the collection fibers 108 via the cladding of the fiber 102 in the vicinity of the hole 104.

Two collection fibers 108 are disposed transversally to the interrogation fiber 102 on each side of the interrogation fiber 102 and in the vicinity of the cladding of the interrogation fiber 102. The collection fibers 108 are also substantially aligned with the hole 104. It should be noted that the cladding may be removed in the vicinity of the hole 104 or along the length of the interrogation fiber 102 for light collection optimization. The collection fibers 108 are used to collect the portion of the scattered light which exits the interrogation fiber 102 via its cladding and the fluorescent light generated by the particles of interest contained in the fluid to be analyzed. The analysis of the light collected by the collection fibers 108 allows for the detection and counting of the particles analytes.

The excitation light reaches the hole 104 and then through the capillary 110 the sample is brought into the interaction volume. Scattered and fluorescence light emitted from particle analytes passing through the interrogation volume is then coupled in the collection fibers 108. The output of each collection fiber 108 can be joined together for a higher signal level. Moreover, this configuration provides substantially uniform signal collection with respect to a homogeneous population of particles. The characteristics of the collection fibers 108 such as diameter, numerical aperture, and the like can be adapted to the dimensions of the hole 104. A larger fiber provides a better alignment but collects more stray light from external hole interfaces. In one embodiment, the numerical aperture has an impact on the fraction of the fluorescent light coupled but is more dependent on the position of the particle in the hole of the excitation fiber.

In one embodiment, the interrogation fiber 102 is a square core optical fiber designed as a beam shaper. While propagating into the square interrogation fiber 102, the intensity distribution of a Gaussian beam emitted by a laser light source and incident on the fluid to be analyzed becomes substantially uniform. This allows to obtain a low coefficient of variation (CV) for a given homogeneous particle population.

In one embodiment, the outer surface of the interrogation fiber 102 is made with a square cross-section or the outer surface has at least one flat region to provide a collection surface. Such a flat collection surface helps in mitigating lensing effects that would be induced by using a standard optical fiber of cylindrical shape.

The region on the outer cladding surface of the interrogation fiber 102 which is adjacent to the light collection unit 106 is referred to as the collection surface 111. In the case of a square cross-section outer surface interrogation fiber, the collection surface 111 is one of the four flat faces of the interrogation fiber 102 and is therefore flat. In one embodiment, the interrogation fiber 102 has a cylindrical outer surface and the collection surface 111 is a surface engraved in the cylindrical outer surface to form a lens which is adapted to collect light from the hole 104. In another embodiment, the collection surface 111 is the typical cylindrical outer surface of standard optical fibers.

The collection surface 111 engraved in the outer surface of the interrogation fiber 102 may be shaped in the longitudinal direction of the interrogation fiber, in its transverse direction or both. Accordingly, the collection surface 111 may be engraved so as to provide a lens of with a spherical, aspherical, conical or cylindrical shape for example. In another embodiment, a diffraction lens or a holographic optical element is engraved. The collection surface may be engraved using laser micro-machining for example.

In one embodiment, the two collection optical fibers 108 are substantially aligned perpendicular to the hole 104 for scattering and fluorescence signal detection. In this configuration, a trade-off may be made between high collection efficiency and low stray light levels. Optical fibers on the collection side may have an impact on the CV performance of the FOFC.

In one embodiment, the collection fibers 108 are multimode fibers of 105/125 µm (Thorlabs™, NJ) with numerical aperture of 0.22. In this case, their contribution to the CV has been calculated to approximately 2%.

In one embodiment, the interrogation fiber has a square core with the following transverse dimensions: $250 \times 250 \, \mu m^2$, the numerical aperture of the interrogation fiber is 0.47, the hole has $125 \times 125 \, \mu m^2$ cross-sectional dimensions and the capillary is a borosilicate square capillary of 115/60 µm (VitroCom™, NJ).

The excitation fiber 102, the hole 104 and the collection fibers 108 are aligned during the fabrication of the fiber optic flow cell 100. Once the different components are secured together, no further optical alignment is needed throughout the lifetime of the fiber optic flow cell 100. The scattering as well as the fluorescence light can then be measured. The use of an optical fiber for excitation and collection reduces mass and volume by eliminating optical components and increases robustness for applications requiring portability.

In one embodiment comprising a square interrogation fiber, the fiber optic flow cell 100 has a substantially sheathless optical configuration which results in a global simplification of the flow cell. As a result, no hydrodynamic focusing is needed as typically used in a flow cytometer. Therefore, no complex plumbing is required in addition to the reduction of the needed quantity of sheath fluid such as distilled water and the reduction of liquid biohazard waste.

In one embodiment, a square hole such as the hole is created using a two-step procedure with a pulsed femtosecond laser and chemical etching. Square holes can be drilled for any adequate diameter of fused silica fiber resulting in an adequate surface quality which reduces stray light level. The square hole as compared with a round hole, for example, not only reduces the CV but also diminishes the level of excitation light (stray light) that is deviated at 90° and reaches the collection optical fibers.

It is noted that while the example apparatus illustrated in FIG. 6 has two collection fibers, one on each side of the interrogation fiber, it is possible to provide a different number of collection fibers depending on the required application. For example, only one collection fiber could be used. Two collection fibers on each side of the hole could also be provided, two for amplitude detection and two others for spectroscopic analysis.

It is also noted that while in the example apparatus illustrated in FIG. 6 the collection fibers are disposed orthogonally to the interrogation fiber, the collection fibers may also be placed transversally relative to the interrogation fiber but with an angle such as a 45° angle for example.

In one embodiment, the collection fibers are replaced by optical light collection systems such as a lens or a group of lenses. The lens or a group of lenses can be located close to the interrogation fiber aligned with the interrogation volume. Light collected by the lens or group of lenses can be directly detected or injected into collection fibers for subsequent detection. An image of the particle passing through the hole can also be made using a lens or a group of lenses. The image can be projected on a camera or a spectrophotometer, for example. The fiber optic flow cell can be positioned on an epifluorescence microscope for direct visualization of the particles in passage through the hole. In order to contribute in the collection, the outer surface of the interrogation fiber may be shaped along the longitudinal direction to act as one or multiple spherical, aspherical, conical or cylindrical lens.

In another embodiment, the fiber optic flow cell comprises a collection fiber on a first side of the excitation fiber and a lens or a group of lenses on a second side for imaging a particle of interest. The collection fiber can be used for camera triggering, for example.

Figure 7:
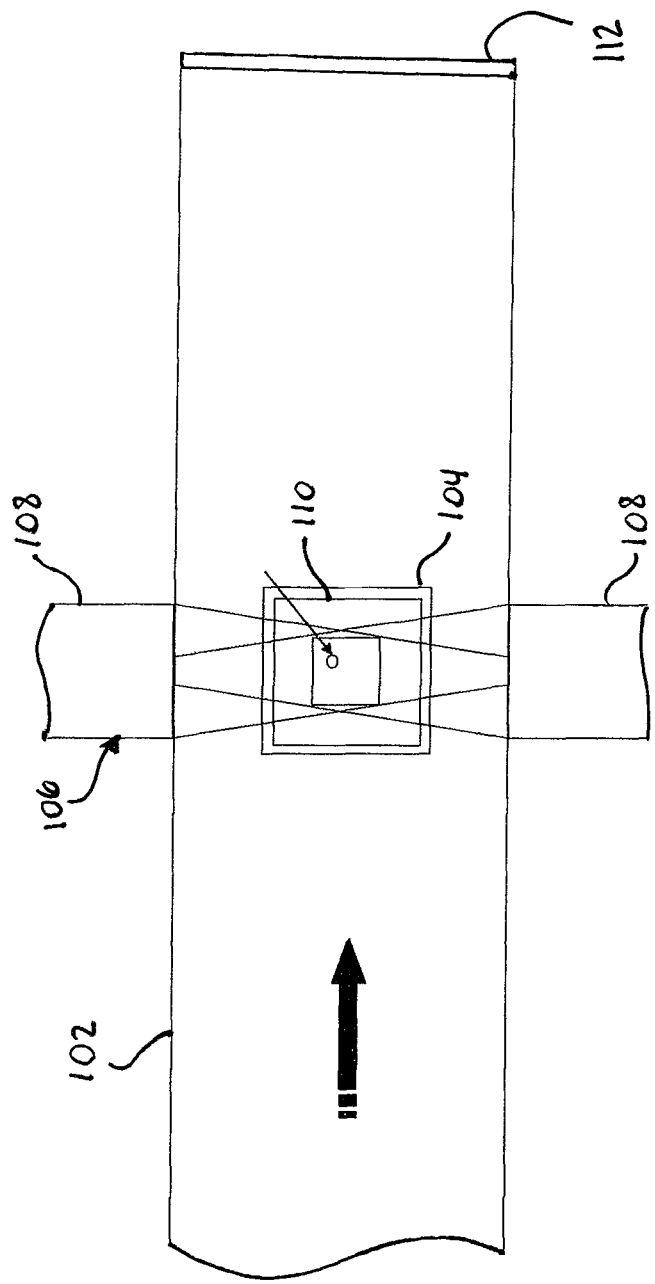
FIG. 7 is a schematic top plan view, fragmented, of another example fiber optic flow cell apparatus to be used in the system of FIG. 1, wherein a mirror is located at the output of the interrogation optical fiber.

FIG. 7 illustrates another embodiment of a fiber optic flow cell apparatus 100 similar to the apparatus of FIG. 6 but further comprising a mirror 112 located at the output of the interrogation fiber 102. The mirror 112 is used to re-inject the excitation light into the interrogation fiber in order to increase the excitation light brought to the interrogation volume. In one embodiment, an increase of optical power up to two fold can be achieved. Different mirror/reflective materials can be used. A thin film mirror or reflective material can be fixed at the output of the interrogation fiber 102. Alternatively, a reflector or the tip of the interrogation fiber itself can be coated with metal as aluminum, gold or a non-metallic reflector such as a dielectric coating, for example.

Figure 8B:
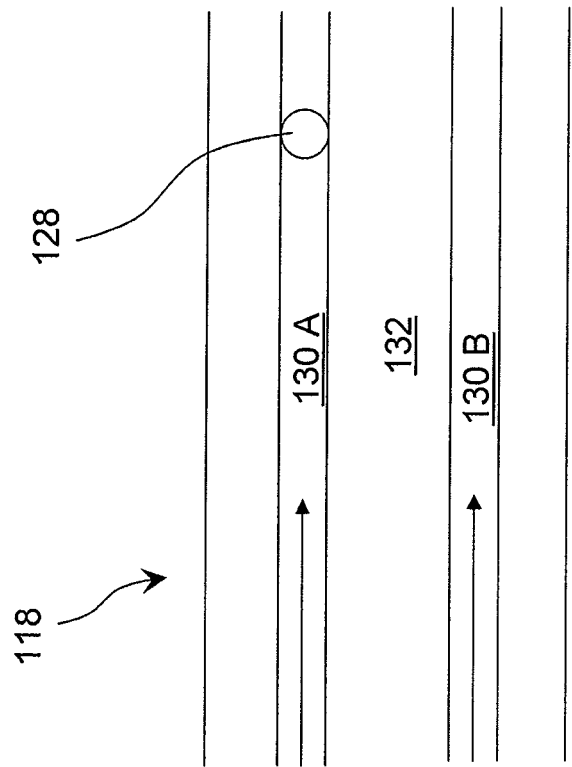
FIG. 8 includes FIG. 8A and FIG. 8B which are front and side cross-sectional views, respectively of an optical fiber with two cores for use in an alternative embodiment of the invention.
Figure 8A:
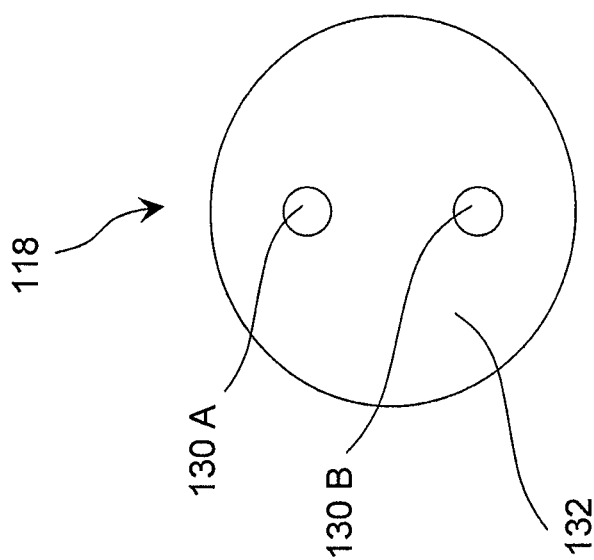

Referring to FIGS. 8A and 8B, another exemplary use of a non-traditional optical fiber is depicted. The double core optical fiber 118 has a first core 130A and a second core 130B. A hole 128 in which the fluid medium is channeled is defined transversally to the first core 130A. When the light traveling within the first core 130A encounters a small body in the hole 128, it goes through a phase shift relatively to the one traveling the second core 130B. The difference of phase between the light traveling the first and second cores could be detected by an interferogram created at the exit of the fiber. Since the interferogram created depends on the size of the small bodies, this method of studying small bodies could prove even more precise than in the case of an optical fiber having a single core. Another method involves the monitoring of the light traveling within the second core for measuring the variation of the light source. Such double core optical fibers are available from INO (Institut National d'Optique), Québec, Canada.

Another alternative which could be used is an optical fiber having two claddings (not illustrated). These optical fibers are called Double Clad Optical Fibers (DCOF). DCOF offer the advantage of having a greater numerical aperture than the more traditional single cladding optical fibers and can thus guide a greater intensity of light, which is typically desired with the present invention. They are generally used for high power optical amplifiers or fiber lasers and consist of two concentric waveguides: one for pump and the other for signal wavelength. The core is single mode and has generally a diameter of few micrometers and is surrounded by a glass cladding of few hundreds of micrometer. The core is doped with rare-earth material for amplification of the signal and then guides the light to be amplified. The first cladding is surrounded by a second cladding to guide the pump light. The second cladding is generally of some low index material to provide a high numerical aperture for the pump. The large area and acceptance angle of the pump cladding allow efficient coupling of high power, low brightness pump diodes. A DCOF could be used with a standard core for a better efficiency of excitation and collection of the fluorescence emission or the forward scattering coming from the interaction of the excitation light with the small bodies. The single mode core can supply a better irradiance and then produce a more intense fluorescence radiance which can be collected by the first cladding of the DCOF having a high numerical aperture. Since the excitation core is not doped with rare-earth, and is contained in the center of the DCOF, significant reduction in autofluorescence can be reached with the DCOF compared with standard multimode optical fiber with the cladding surrounded by a fluorescent coating such as nylon and tefzel. Double clad optical fibers are also available from INO.

Turning back now to FIG. 2, in some applications where the small bodies 34 are biological specimen containing naturally occurring fluorophores such as riboflavin or NADH (nicotinamide adenine dinucleotide), the small body 34 emits endogenous fluorescence which is stimulated by exposure to light at certain wavelengths, typically in the UV spectrum. This is true for many types of cells and microorganisms. In such cases, a portion of the endogenous fluorescence emitted by the small body could be guided within the optical fiber 18 and be detectable at the exit of the optical fiber 18 by a suitable detection system 40, to provide specific information about the small body 34 under study, especially when a high intensity of light affects the small body 34. In order to generate this fluorescence, use would be made of a Light Emitting Diode (LED) with peak emission within the UV spectrum, and corresponding to the stimulation wavelength, as a light source. In order to acquire information on the status of the small body 34, the light source 14 must be selected adequately and take into account the type of small body 34 to study. Typically, one or more LEDs 14 are used. Preferably, the LEDs 14 are optically coupled to the optical fiber 18 via a known optical injection device such as, for example, a microscope focusing lens assembly. Alternative light sources that can be used include laser diodes, for example.

In one application of the present invention, information as to the vitality state (if it is alive or dead) of bacterium 34 is obtained using the apparatus. The structure and composition of dead bacteria is different from that of live bacteria. For example, the membrane of dead bacteria is generally perforated, and no longer achieves impermeability. The perforated membrane thus allows contact between molecules of specific dyes and internal constituents of dead bacterium. Hence, dyes can be used to color proteins or other nucleic acids in dead bacteria, whereas other dyes have a coating action onto the membrane of living bacteria. Preferably, fluorochrome dyes which emit fluorescent radiation when stimulated at certain wavelengths are used. The preferred dyes are the penetrating action Marina Blue™ dye with stimulation wavelength of 365 nm and fluorescent emission wavelength of 460 nm, and the Prodan™ coating action dye with stimulation wavelength at 355 nm and fluorescent emission wavelength at 525 nm, both available from Invitrogen (www.invitrogen.com). The dyes produce different effects on live and dead cells when submitted to the appropriate UV radiation, and emit fluorescence light at different wavelengths. Part of the fluorescence light emitted is guided in the optical fiber and can be detected at an exit thereof. By studying the spectrum of the light exiting the optical fiber 18, it is thus made possible to determine if the cells are alive or dead. In this specific application, a LED 14 with peak emission at 365 nm and a power of 100 mW is believed to be particularly effective in obtaining the desired fluorescence intensity. Such a LED 14 is available from Nichia American Corporation. Other dyes can alternatively be used in combination with a light source of corresponding wavelengths, for example, a laser diode emitting light in the visible spectrum could be used with fluorochrome dyes which have an absorption wavelength located in the visible spectrum.

Figure 9:
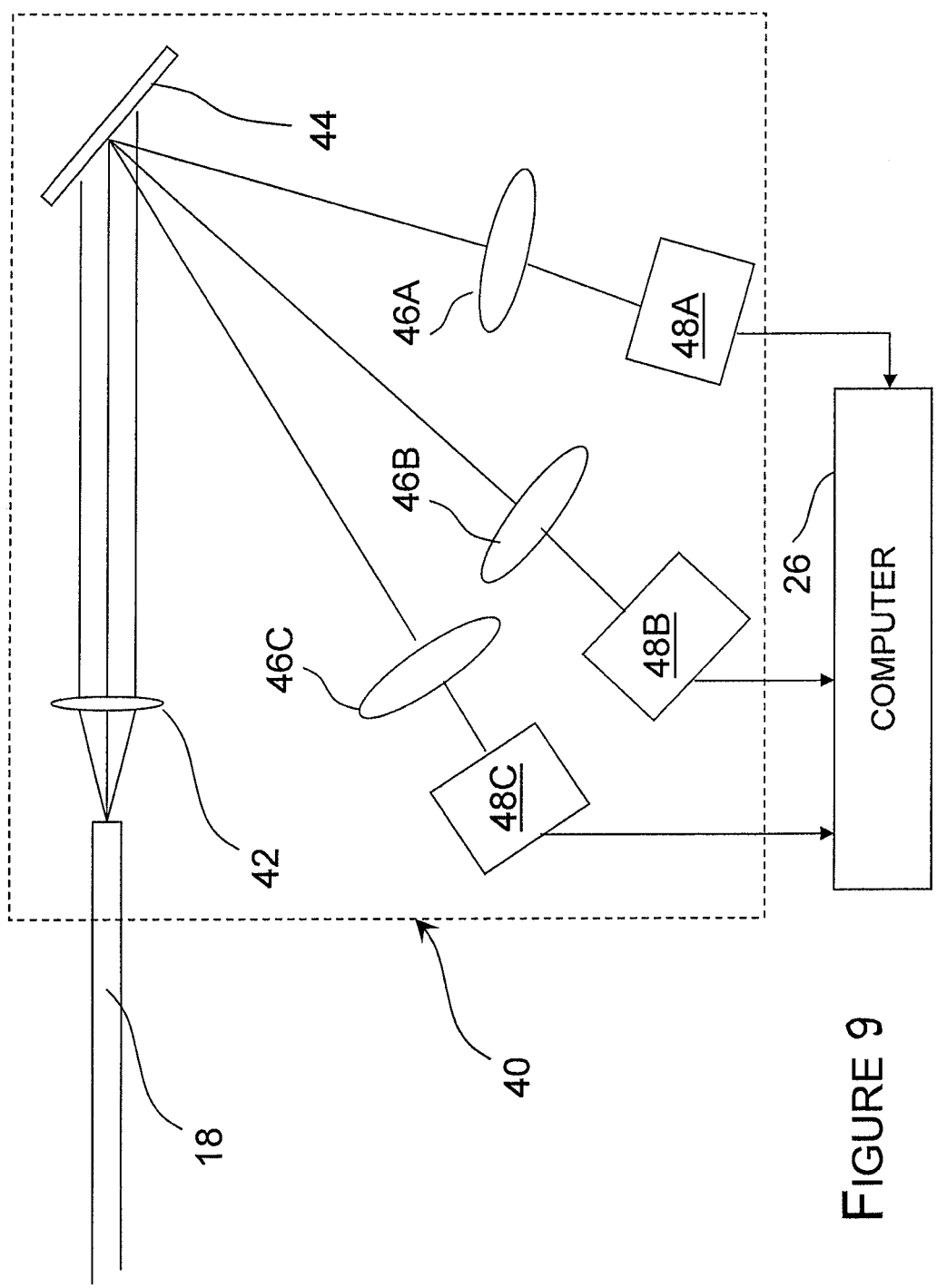
FIG. 9 is a schematic view of a detection system of the system of FIG. 1.

FIG. 9 shows an exemplary embodiment of the detection system 40 (see also FIGS. 1 and 2) adapted to measure the fluorescence signal and detect the vitality status of bacteria. The light exiting optical fiber 18 is fed through a collimation lens 42 and directed to a diffraction grating 44. After diffraction, the intensities at three wavelengths are detected: a fluorescence wavelength λ emitted by dead bacteria, a fluorescence wavelength B emitted by living bacteria, and a wavelength C corresponding to the wavelength of the light source (in this case a LED). Each wavelength is diffracted at a different angle by the diffraction grating 44. A first focusing lens 46A and photodetector 48A assembly is used to measure the exiting intensity at wavelength A, a second such assembly is used to measure the exiting intensity at wavelength B, and a third similar assembly is used to measure the exiting intensity at wavelength C. Preferably, the photodetectors 48A, 48B, and 48C are connected to a computer 26.

Figure 10:
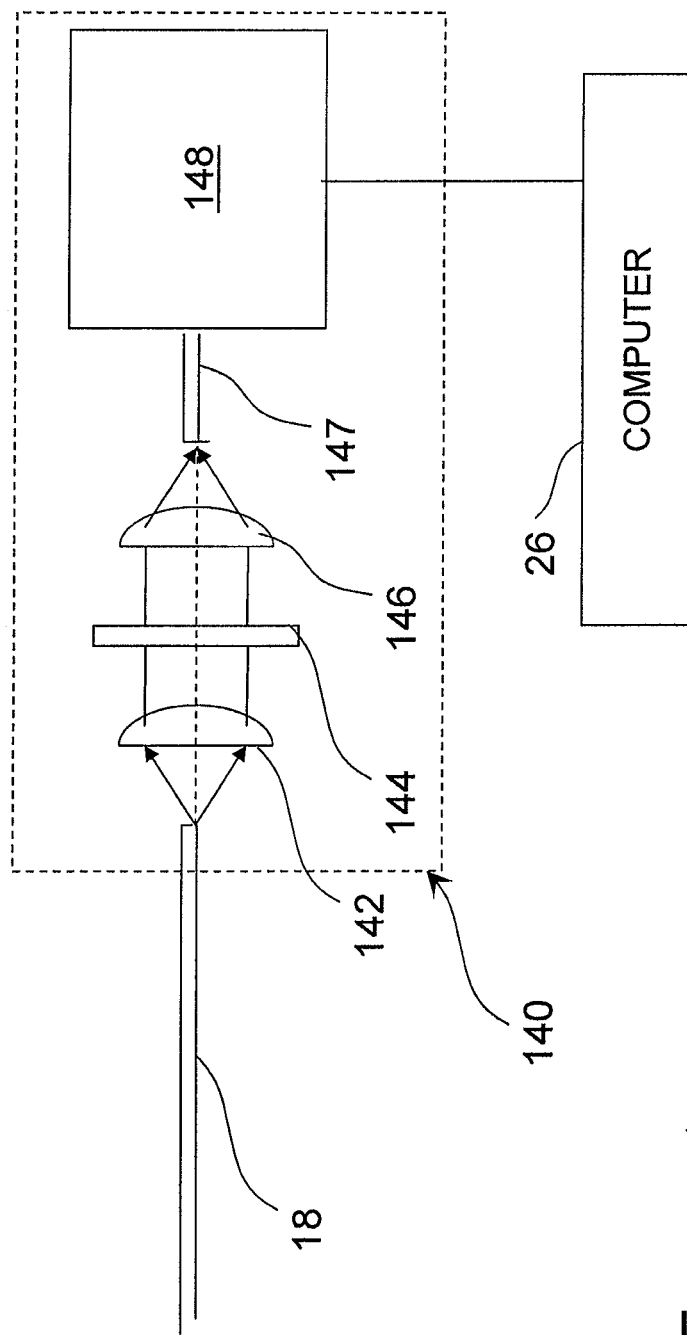
FIG. 10 is a schematic view of an alternative detection system to the detection system of FIG. 8.

FIG. 10 depicts an alternative detection system 140 to the detection system 40 of FIG. 9. The alternative detection system 140 includes a first collimating lens 142 for collecting the light exiting the optical fiber 18; a fluorescence filter 144; an injection lens 146 receiving the light once passed through the filter 144; and a spectrometer 148 having an optic fiber 147 for receiving the light beam concentrated by the injection lens 146. This detection system 140 is suited in the fluorescence study of a homogeneous solution without small bodies and passing through the hole of the optical fiber 18. The filter 144 is used to block out the wavelengths of the source and let fluorescence emanated from the homogeneous solution pass through.

It is to be understood that many other suitable detection systems known by those skilled in the art can be used in view of particular applications, for example, a fiber Bragg grating can be used to separate wavelengths with a single-mode optical fiber.

Figure 11A:
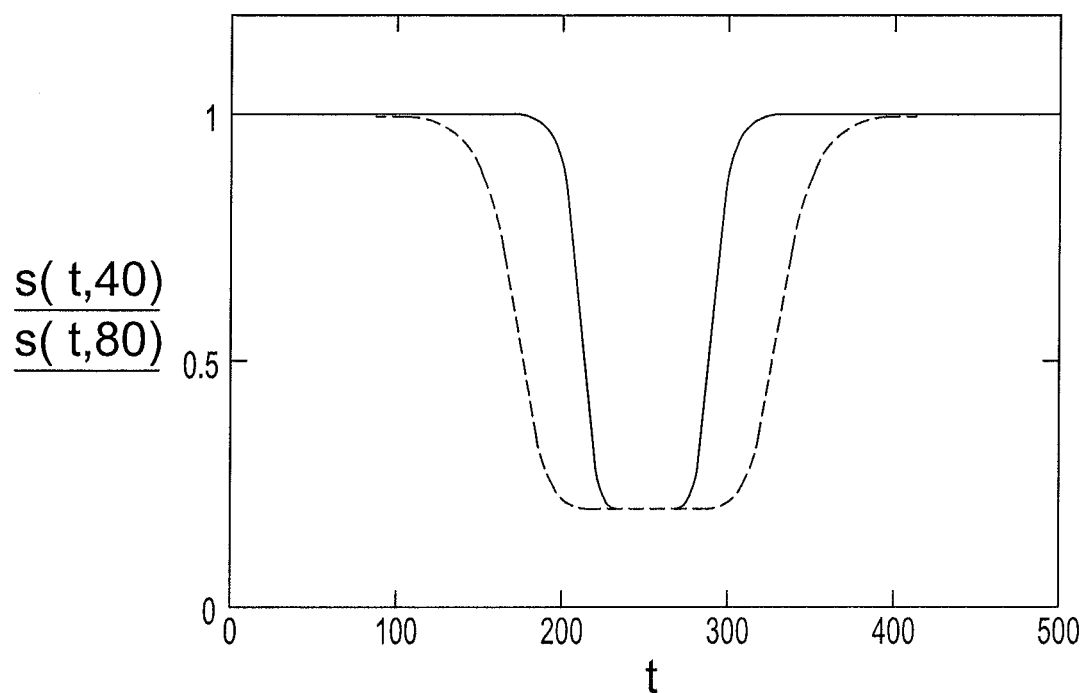
FIG. 11A shows a typical graph illustrating the variation of the quantity of light detected when two bacteria of same size but different lengths are illuminated.
Figure 11B:
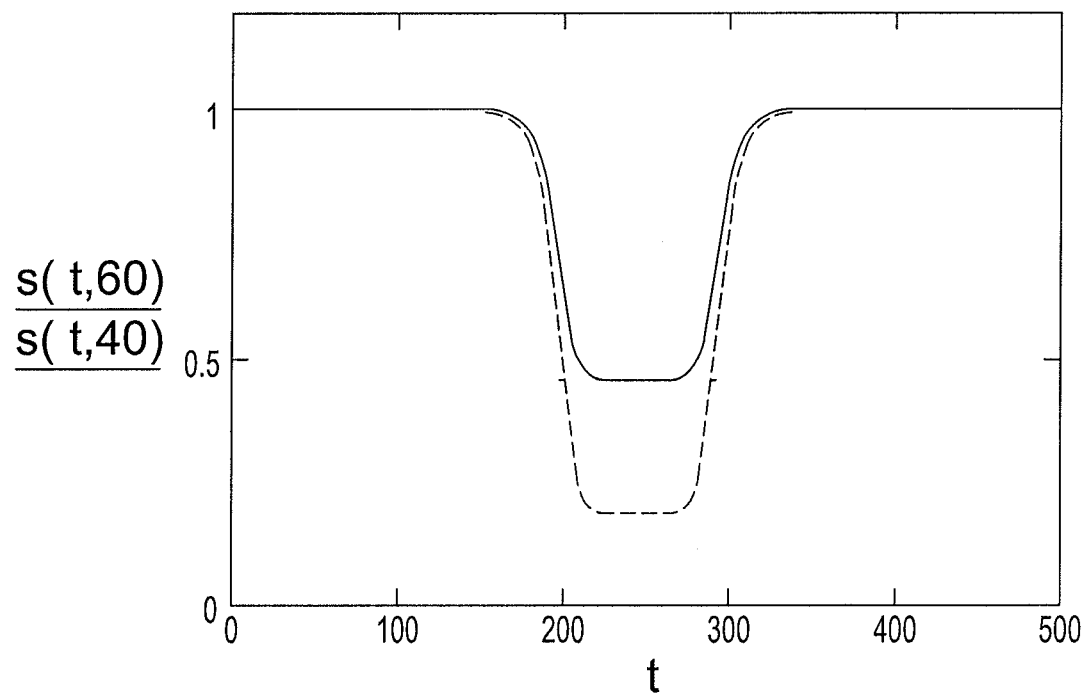
FIG. 11B shows a typical graph illustrating the variation of the quantity of light detected when two bacteria of same length but different sizes are illuminated.

By assessing the detected intensity at wavelength C, the presence of a bacterium in the hole is determined and its size is estimated. Additionally, it is determined whether the bacterium is dead or alive (the vitality status) by assessing the measured intensities at wavelengths A and B. Preferably, the output of photodetector 48C can be connected to an acquisition card of the computer 26. The variation of the electric signal of the photodetector 48C with time is stored in the computer memory during the flow of the fluid medium. Assuming that the size and the length of the bacteria are taken, respectively, parallel and perpendicular to the optical axis of the optical fiber, the normalized electrical signal varies as a function of time and the variation depends on the size and length of the bacteria intersecting the light beam, as shown in FIGS. 11A and 11B. Since the quantity of light scattered depends on the size of the bacteria, the amplitude variation of the electrical signal is indicative of the size of the bacteria. Further, the duration of the amplitude variation is indicative of the length of the bacteria when the flow rate is set at a fixed value. Hence, two bacteria of same size but of different lengths are responsible for the superposed signals illustrated in FIG. 11A, whereas two bacteria of different sizes but of same length are responsible for the superposed signals of FIG. 11B. A relatively simple algorithm can calculate the first derivative of the signal s (t, a), where t and a represent the time and the length of the bacteria respectively, and activate a timer, comparators, and counters to determine the duration and amplitude of the electrical impulses. In this way, an impulsion of given amplitude and given duration would be associated to a bacterium of given size and given length intersecting the light beam. In this preferred example, a single algorithm suffices to indicate the presence, size, and length of the bacterium, and the detection system 40, acquisition card, and computer 26 serve as both a presence detector and a dimension detector. The triple assessment can alternatively be made by two or three algorithms provided in the computer 26 using a single signal and acquisition card, or a separate presence detector and dimension detector, having the corresponding functions, can be used instead. The dimension detector can also be provided as separate size and length detectors. Calibration of the instrument can be done with micro-spheres of known diameter, like it is the case in other commercial flow cytometers.

Figure 11C:
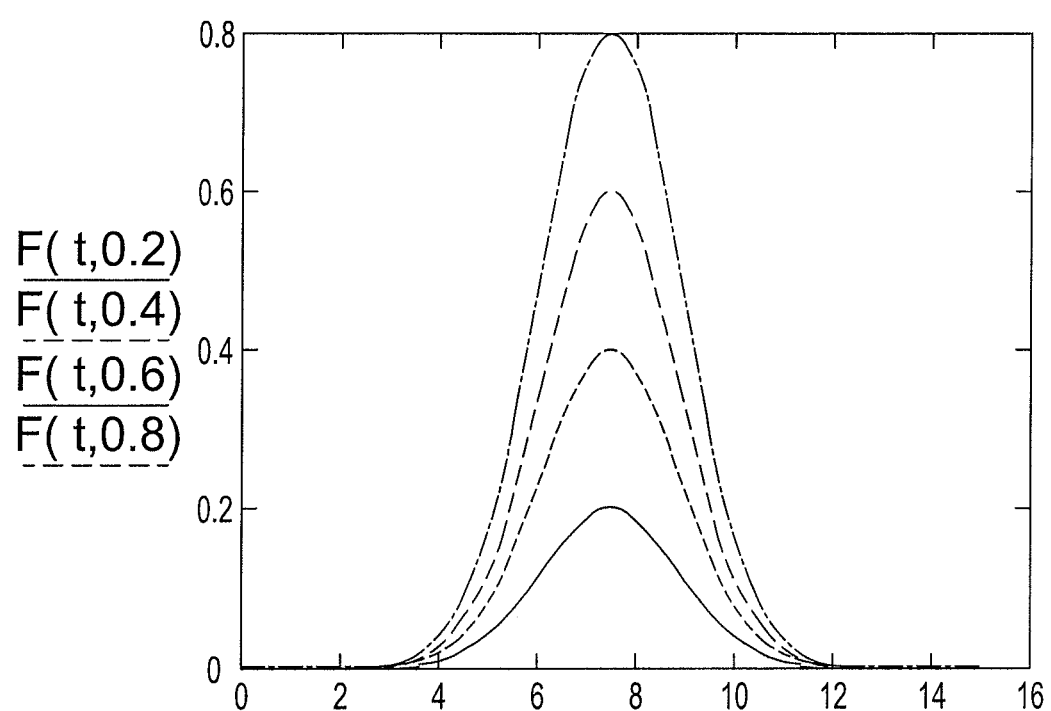
FIG. 11C illustrates the electric pulses produced by the fluorescence of bacteria labeled with fluorophores.

For a living bacterium, the signal acquisition from the output of photodetectors 48C and 48B are practically simultaneous, and the function of detecting status is carried out using both signals. The fluorescence signal F (t, b), where t represents the time, at the exit of photodetector 48B can take the shape of an electric impulse such as depicted in FIG. 11C. For bacteria smaller than the diameter of the optical fiber core, the amplitude b of this signal depends of the number of fluorophores which are attached to the bacteria. If the dyeing of the bacteria is successful, the amplitude of this signal will vary as a function of the size of the bacteria. Therefore, the simultaneous detection of an electrical impulse at the exit of photodetectors 48C and 48B is indicative of the passage of a living bacterium across the light beam in the optical fiber. Similarly, the passage of a dead bacterium is indicated by simultaneous impulses at the exit of photodetectors 48A and 48C. Standard micro-spheres labeled with a fluorochrome of absorption wavelength compatible with the peak wavelength of the light source can be used to calibrate photodetectors 48B and 48A. Preferably, the corresponding algorithm to determine the status is provided in the computer 26, and is done in combination with the dimension and presence determination. However, a separate status detector can be used.

Figure 12:
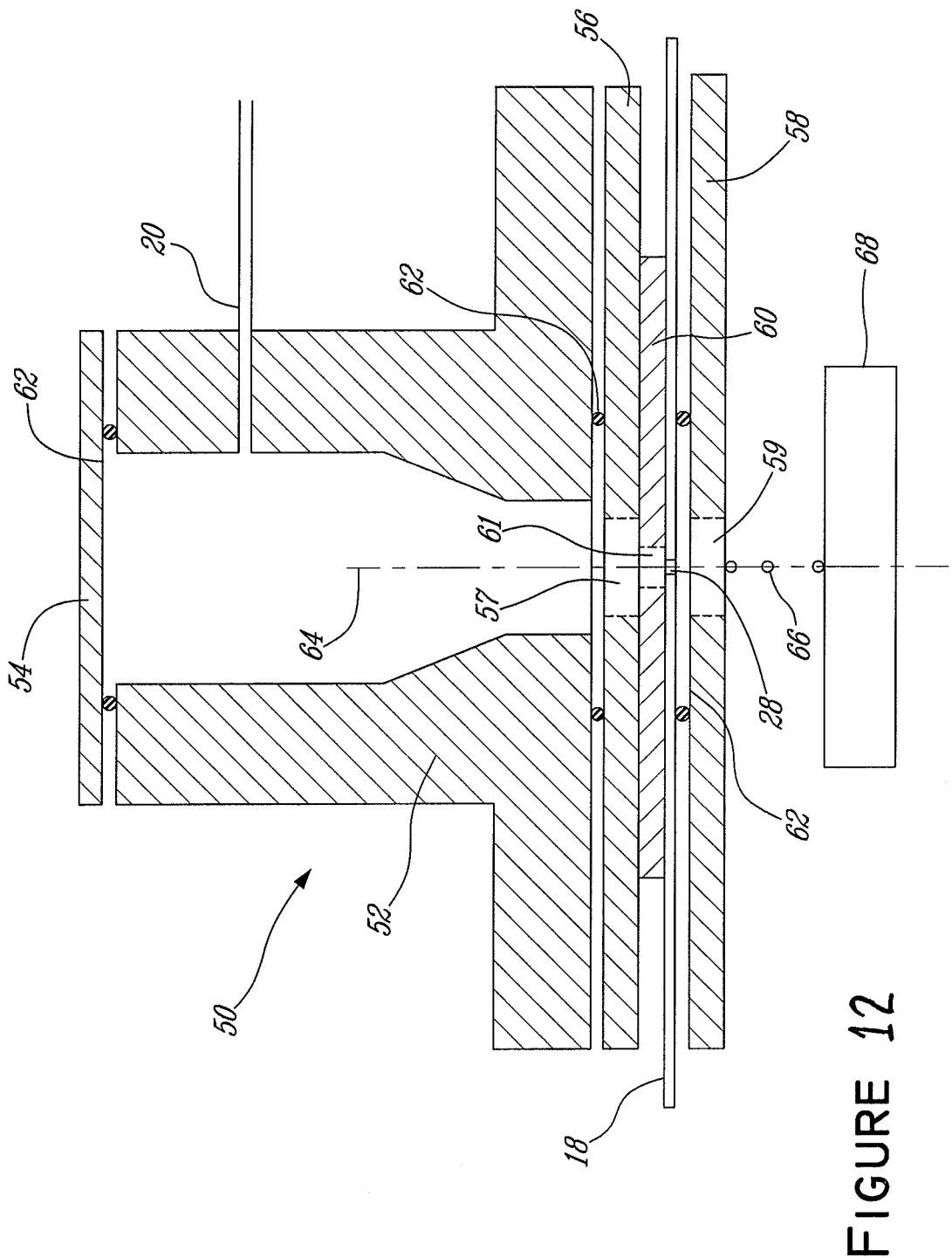
FIG. 12 is a cross-sectional view of a channeling system of the apparatus of FIG. 1.

FIG. 12 shows an exemplary embodiment of the channeling system 50. A container 52 with a cover 54 contains the fluid medium in which the small bodies are held. Pressure is transmitted into the container 52 via the pressure inlet 20. The optical fiber 18 is held between a container plate 56 and protector plate 58 through which coaxial container apertures 57 and protector plate aperture 59 are defined. Preferably, container plate 56 is made of steel, and has a container aperture 57 of 500 μm. A glass plate 60 of 150 μm thickness with an intermediate aperture 61 of a diameter between container aperture 57 and that of the hole 28 in the optical fiber 18 is used between container plate 56 and optical fiber 18 to channel the fluid medium by successively funneling it more precisely into the region of light propagation. Intermediate aperture 61 is preferably of 75 μm diameter, and the portion of the optical fiber 18 having the hole 28 is held and sealed thereagainst by glue applied around intermediate aperture 61.

Epotek produces a variety of glues with low autofluorescence that can be used to bond optical elements. A gasket 62 having a diameter approaching 3 mm is preferably used between the optical fiber 18 and protector plate 58. A gasket 62 is also used between container plate 56 and container 52, as well as between container 52 and cover 54. Hence, container aperture 57, protector plate aperture 59, intermediate aperture 61 and hole 28 are coaxially aligned along a channeling axis 64. Once it has passed through the hole 28, the fluid medium 36 creates drops 66 which fall into a recipient 68. The frusto-conical shape of the hole 28, which is shown exaggerated in FIG. 2, slightly contributes to the funneling action. The pressure to the channeling system is fed from a pressure tank 22, and is controlled by a computer 26 via a pressure controller 24. Preferably, the pressure tank contains dry air and the computer 26 controls the pressure controller 24 depending on the output light detected by the detection system 40. Any suitable alternative channeling system 50 can be selected and used by those skilled in the art realizing alternative embodiments of the invention. Typically, those realizing alternative funneling systems will select alternatives which ensure precision of entry of the fluid medium in the hole 28.

Figure 13:
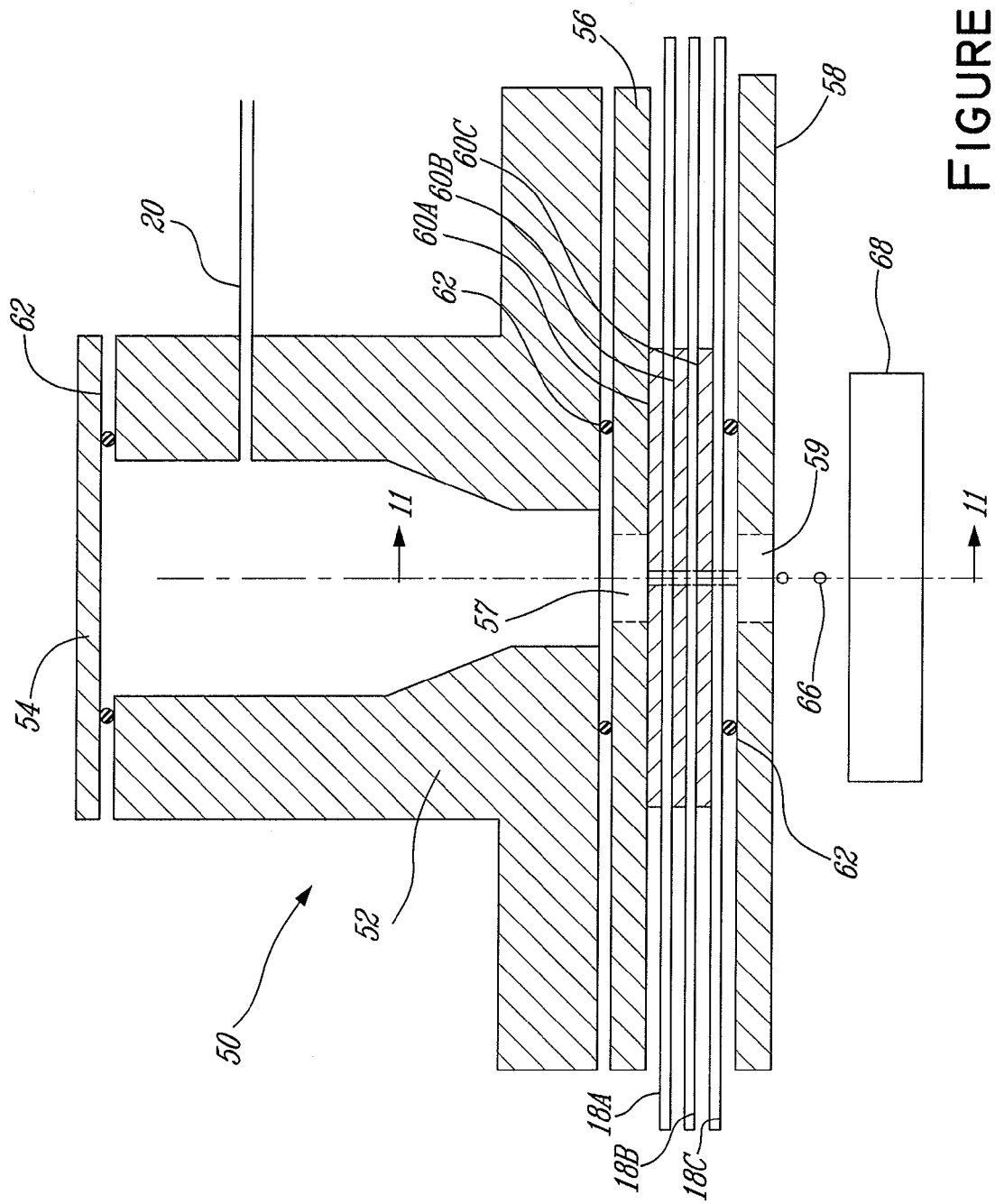
FIG. 13 is a cross-sectional view of an alternative to the channeling system of FIG. 12, adapted to three superposed optical fibers.
Figure 14:
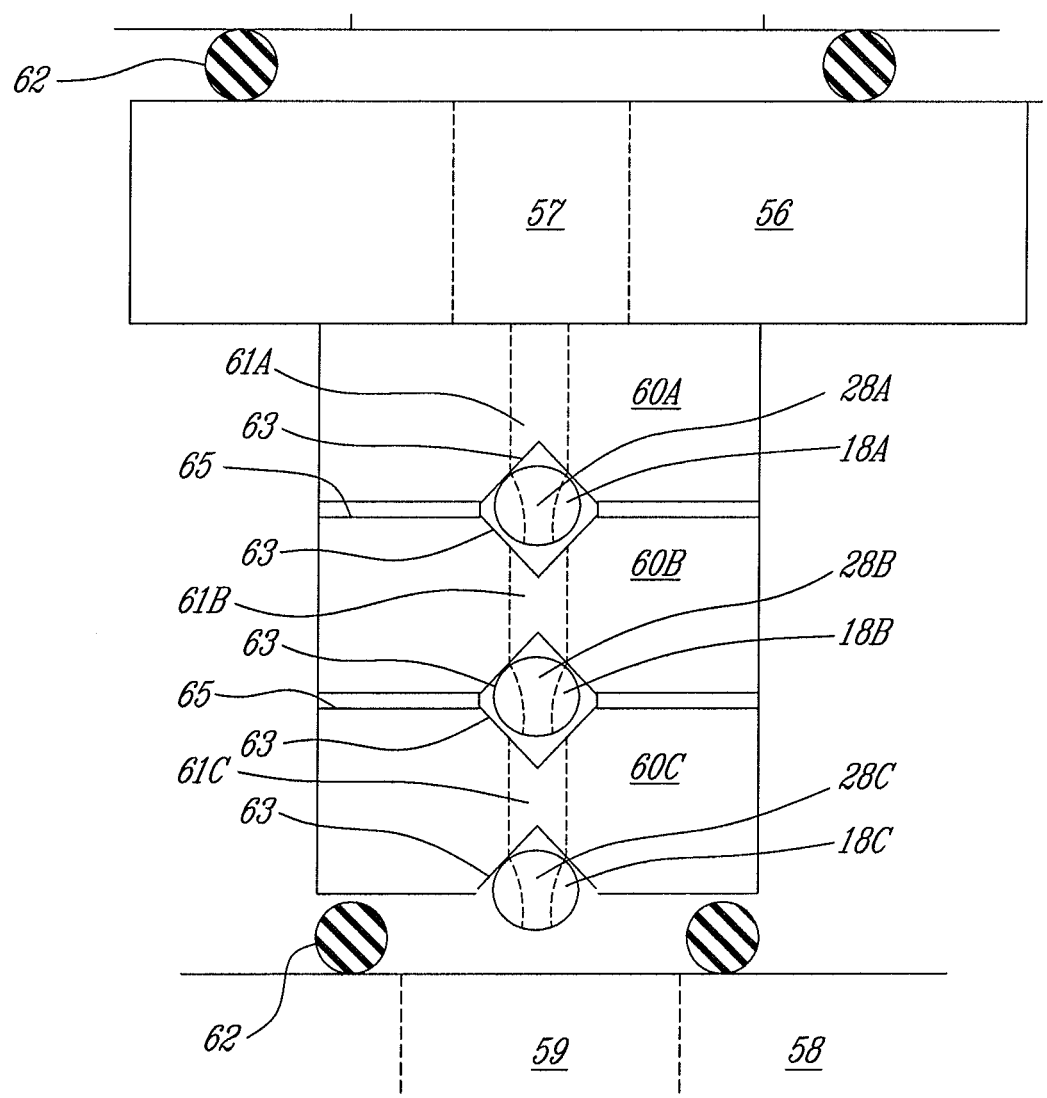
FIG. 14 is a cross-sectional view taken along cross section lines 16-16 of FIG. 10.

FIG. 13 illustrates an alternative to the channeling system where the fluid medium intersects three successive optical fibers 18. Three glass plates 60A, 60B, 60C act as intermediary between the fibers, and between the first optical fiber and the upper plate 56. The funneling action into the successive optical fibers 18A, 18B, 18C is illustrated in FIG. 14 where it is shown that a channel is defined between the container aperture 57, and the aperture 61A in the first glass plate 60A, between first aperture 61A and the hole 28A in the first optical fiber 18A, between the first hole 28A and the second aperture 61B, and successively through the holes in the second and third optical fibers 18B and 18C. The glass plates 60A, 60B, 60C are preferably melted silica lamellae which are made with grooves 63 to make it easier to position the optical fibers relatively to the channel. The successive glass plates 60 are glued together via spacers 65.

Using successive optical fibers provides the following advantages. A light source of a different peak wavelength can be used in each successive optical fiber 18, which allows using fluorochrome dyes with different absorption wavelengths, for example. Further, knowing the distance between the successive fibers, the flow rate of the fluid medium can be measured by adding micro-spheres marked with a specific dye, and measuring the time elapsed between the impulses in the intensity of light detected at the exit of the corresponding fibers. In fact, the impulse detected at the exit of the first optical fiber 18A can be used to trigger a light pulse from the light source of a successive optical fiber. In this application, a pulsating emission LED can thus be used to produce a concentrated pulse of high intensity light directly onto an oncoming bacterium. This can be particularly advantageous when attempting to generate fluorescence outputs which necessitate a high intensity of light. The bacteria will thus receive the high intensity light pulse and the fluorescence signal detected at the exit should be proportionally increased.

Figure 15:
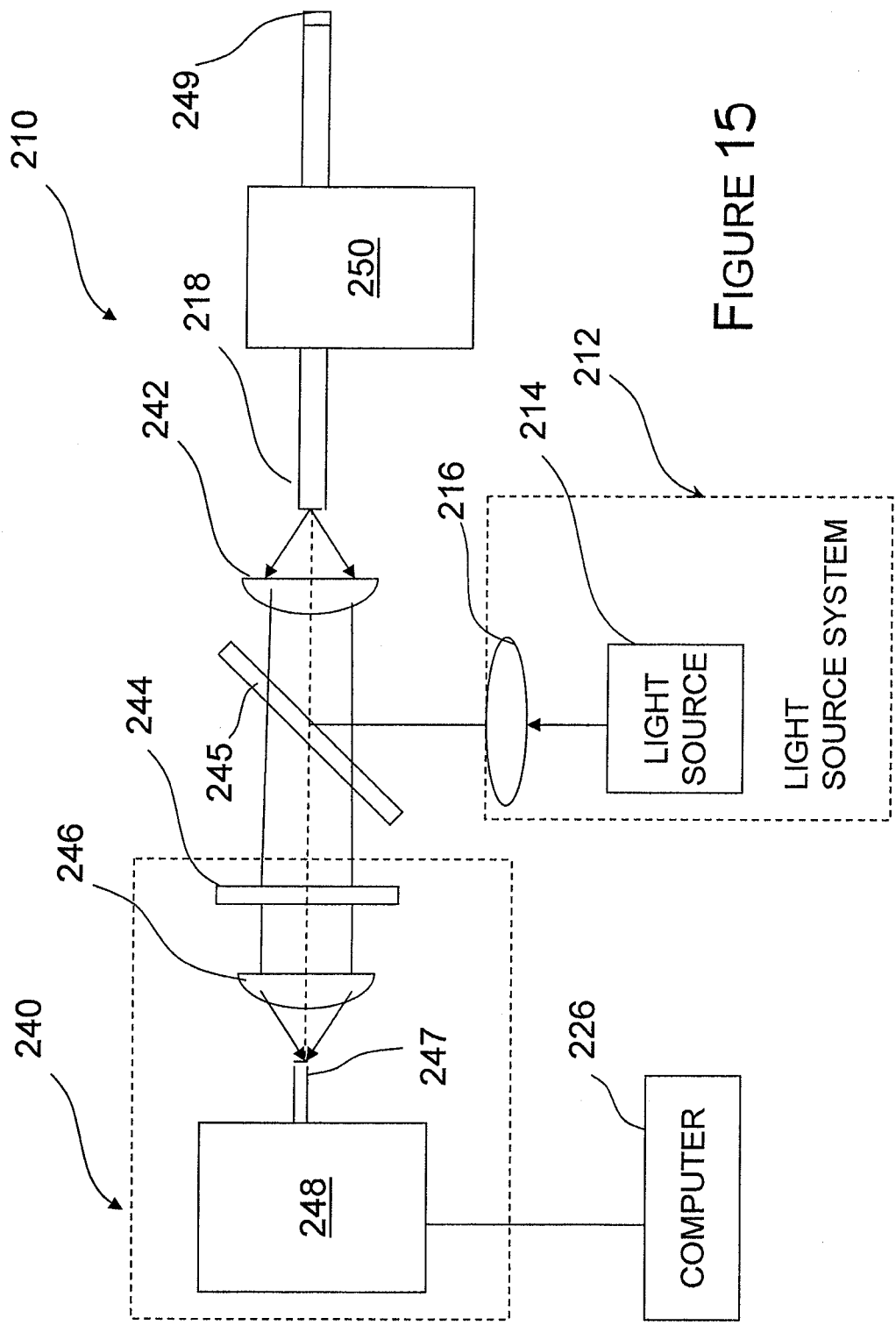
FIG. 15 is a schematic view of an alternative to the system of FIG. 1.

Turning now to FIG. 15, an alternate embodiment to the apparatus described above is shown. Tests have shown that using the apparatus described above, a variation of the optical signal is measured when particles cross the passage in the optical fiber. However, it remains that there are undesirable variations in the electrical signal. These variations are caused, for example, by the passage of particles following different trajectories in the hole of the optical fiber and also by electronic noise, since the quantity of detected light remains relatively low. Hence, to minimize the variations caused by the passage of the particles following different trajectories, a system mounted in reflection instead of a system mounted in transmission can be used as will now be described using reference numerals in the 200 series.

The alternate apparatus 210 also includes a light-source system 212, an optical fiber 218, a channeling system 250 and a detection system 240. However, it is seen that both the light-source system 212 and the detection system 240 are connected to the same end of the optical fiber 218. In particular, a dichroic filter 245 is used. In use, light from the light-source system 212 is reflected by the dichroic filter 245 and fed into the optical fiber 218. The light then crosses an interaction volume in a passageway in the optical fiber where the fluid is channeled by the channeling system 250. The light interacts with the fluid. Fluorescence emitted in the interaction volume will then travel back in the optical fiber 218 and across the dichroic filter 245 to be detected by the detection system. A metallic layer 249 can be used at the other end of the optic fiber 218 to reflect light. Fluorescence emanated in the optical fiber in the direction of the metallic layer will then be reflected back across the hole, out the optical fiber 218 and will also be detected by the detection system 240. Light at a wavelength of that emitted by the light-source system which is reflected back from the metallic layer 249 will be reflected by the dichroic filter 245. This latter example of an alternate configuration is particularly interesting to measure fluorescence of particles.

Figure 16:
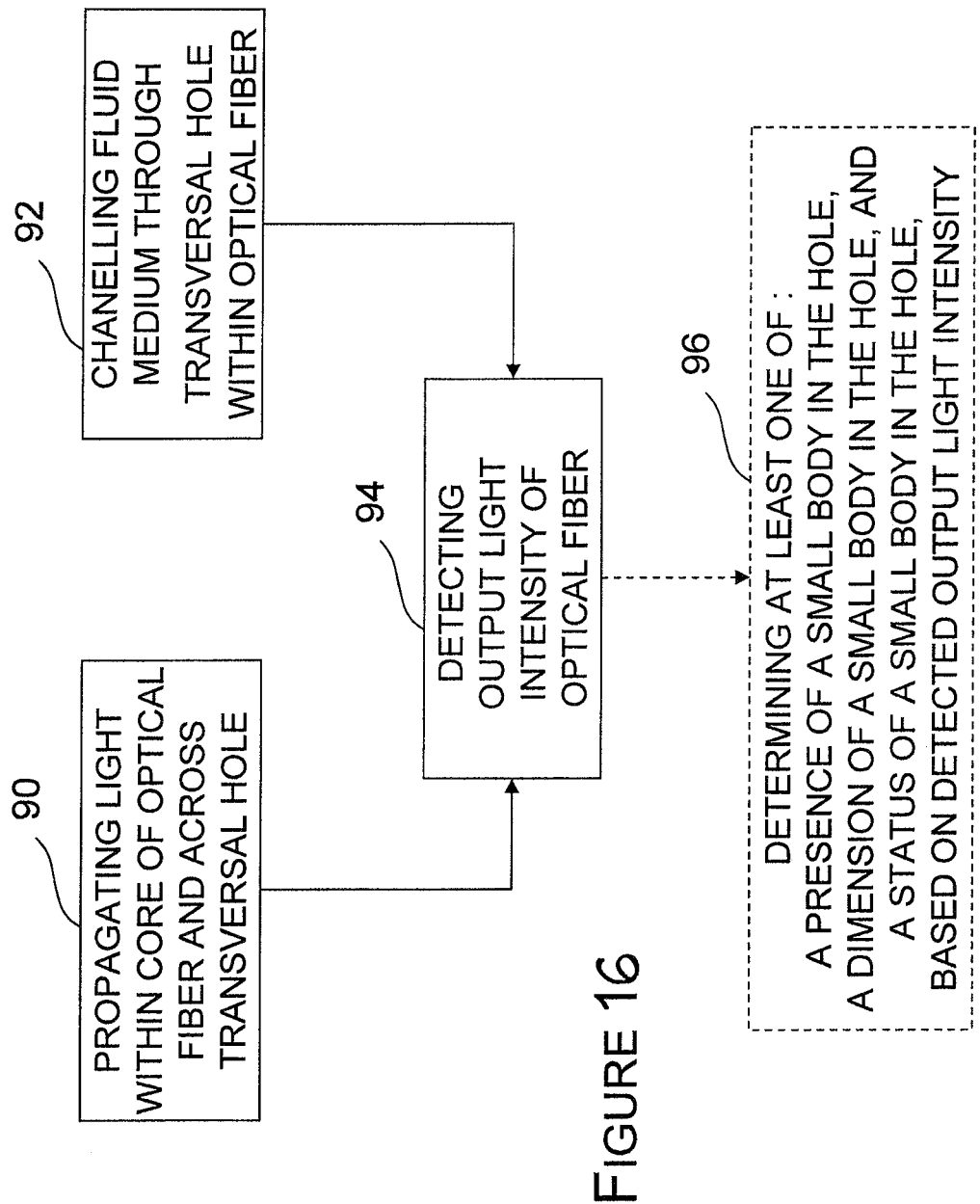
FIG. 16 is a flow chart illustrating the main steps of a method of analyzing small bodies in a fluid medium, in accordance with one other embodiment of the present invention.

FIG. 16 presents a method for analyzing small bodies in a fluid medium in accordance with another embodiment of the present invention. The method includes channeling 92 the fluid medium containing the small bodies in the hole traversing transversally an optical fiber, propagating 90 a light into the core of the optical fiber and across the hole and generating an output light intensity, and detecting 94 the output light intensity. The method may further comprise determining 96 at least one of the following: the presence in the hole of a small body, the size of a small body in the hole and the vitality status of a small body in the hole, based on the detected output light intensity.

The apparatus can be considered as a flow cytometer in which the fluid medium is channeled within the transversal hole of the optical fiber, and the light is guided within the optical fiber and intersects the path of the fluid medium in the hole. The small bodies are analyzed by detecting the output of light exiting the fiber after it has intersected the fluid medium.

Figure 17:
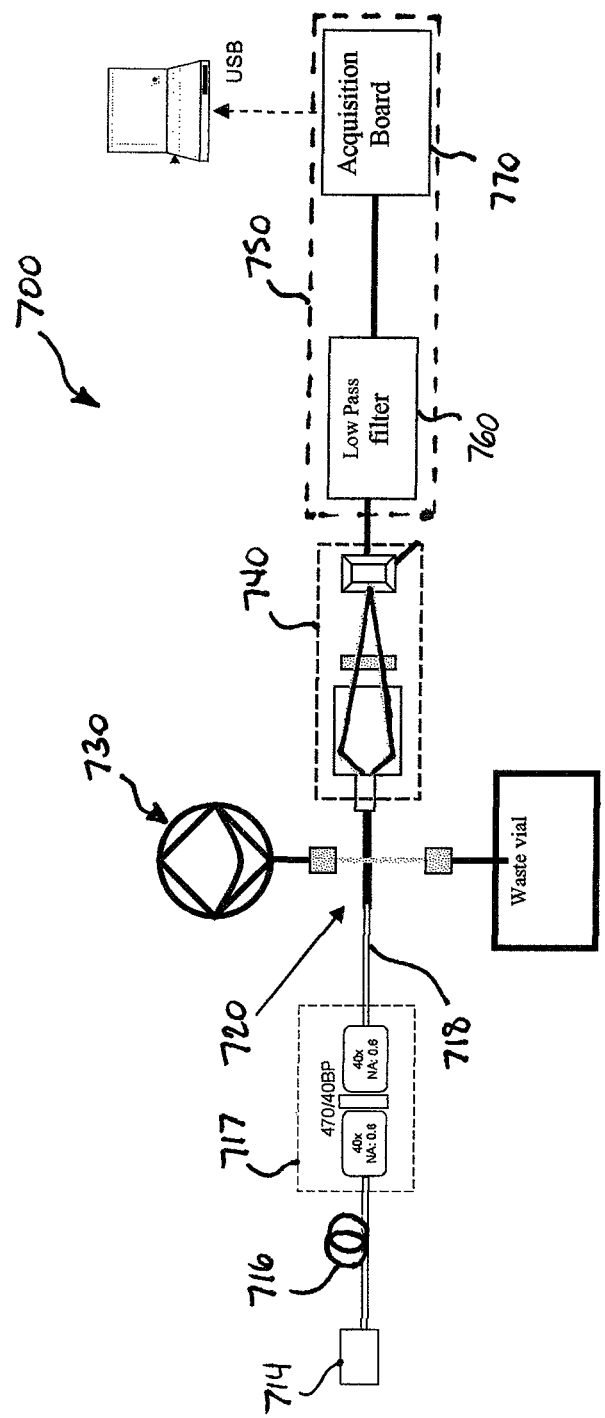
FIG. 17 is a block diagram illustrating a flow cytometer system comprising an in-line filtering module.

FIG. 17 illustrates a fiber optic flow cytometer 700 comprising an in-line filtering module. The fiber optic flow cytometer 700 comprises a light source 714, a beam shaping optical fiber 716, a filtering module 717, an interrogation fiber 718 with a flow cell 720, a channeling system 730, a detection system 740 and an acquisition system 750, comprising a low pass filter 760 and an acquisition board 770. The filtering module 717 is positioned between the light source 714 of excitation light and the flow cell 720 in order to reduce or substantially eliminate background light which may deteriorate the quality of fluorescent signal generated by the passage of particle analytes in the region of interest. A beam shaping optical fiber 716 consisting, for example, of one or a few meters of the interrogation fiber is used in order to render uniform light from the light source 714. This shaped light is then filtered using the in-line filtering module 717. The filtered excitation light is then injected into a short length of interrogation fiber 718, typically less than 1 m and 0.3 m in this case, before propagating through the passageway, i.e. in the flow cell 720. Light resulting from the interaction between the excitation light and the particle analytes is detected using the detection system 740 and acquisition system 750.

In one embodiment, the light source 714 comprises a LED. A LED generally has a large emission spectrum which often interferes with the fluorescence detection channel. For that reason, the emission spectrum of the LED should be cleaned up. In one embodiment, the in-line filtering module 717 comprises a first collimator, a laser-line filter and a second collimator. The use of a LED improves the performance for flow cytometry by reducing the coefficient of variation. The characteristic non-coherence of a LED light source prevent multiple light propagation modes from interfering together, thereby generating uniform excitation light. The uniform excitation light provides a uniform fluorescent signal from particle(s) contained in a homogeneous particle population.

Although the preferred embodiment of the invention described referred most specifically to the study of bacteria in water, one skilled in the art will understand that the invention is adapted to study other small bodies in other fluid mediums. For example, alternative small bodies can be cells, other biological specimen, particles in solution, etc., whereas alternative fluid mediums can be other liquids having a relatively low viscosity, like alcohol, milk or blood based liquids. One will also understand that the fluid medium can also alternatively be a gas such as air in which small particles in suspension are studied by crossing a light beam guided within an optical fiber. In this latter case, the channeling system should be sealed. Further, as it was seen above, the system could be used to analyze a homogeneous fluid solution without small bodies. Such a homogeneous fluid preferably includes fluorophores and is studied by the fluorescence it emits and which is guided within the exiting light.

The embodiments of the invention described above are intended to be exemplary only. The scope of the invention is therefore intended to be limited solely by the scope of the appended claims.

What is claimed is:

1. An apparatus for use in analyzing a fluid with particle analytes comprising:
    a light source unit for providing an excitation light;
    an interrogation optical fiber optically connected to said light source unit for receiving said excitation light and comprising:
        an optical core extending along a longitudinal axis of said interrogation optical fiber for guiding said excitation light, said optical core being multimode and being adapted to shape said excitation light with a substantially uniform spatial illumination over a cross-section of said optical core; and
        a passageway extending throughout said interrogation optical fiber in a transverse direction relative to said longitudinal axis of said interrogation optical fiber such that said passageway intersects said optical core, said passageway for circulating said fluid across said interrogation optical fiber and being shaped such that circulating particle analytes cross said excitation light as said excitation light propagates through said passageway, an intersection of said fluid in said passageway and said excitation light defining an interaction volume wherein a result of an interaction of said excitation light and said particle analytes is representative of a parameter to be analyzed, said passageway being configured relative to said optical core such that said particle analytes are exposed to said excitation light for a generally same duration of time while circulating in said passageway;
    a channeling unit connected to said passageway to circulate said fluid and its particle analytes through said passageway; and
    a light detection unit for detecting said result of said interaction of said excitation light with said particle analytes.

2. The apparatus as claimed in claim 1, wherein said light source unit comprises a light emitting diode.

3. The apparatus as claimed in claim 1 or 2, wherein said light detection unit is connected to an output of said interrogation optical fiber for detecting a change in said excitation light resulting from said interaction.

4. The apparatus as claimed in claim 1 or 3, further comprising a light collection unit located along said interrogation optical fiber in the vicinity of said passageway and in a transverse orientation relative to said longitudinal axis of said interrogation optical fiber, for collecting light resulting from said interaction of said excitation light with said particle analytes of said fluid.

5. The apparatus as claimed in any one of claims 1 to 4, wherein said optical core has a substantially rectangular cross-section.

6. The apparatus as claimed in claim 5, wherein said passageway has a substantially quadrilateral frustum shape.

7. The apparatus as claimed in any one of claims 1 to 6, wherein a numerical aperture of said interrogation optical fiber and a central wavelength of said excitation light are such that a speckle appearing in said excitation light has a size that is smaller than a size of said particle analytes.

8. The apparatus as claimed in claim 7, wherein a number of transversal modes of propagation of said excitation light in said interrogation optical fiber is at least 1000.

9. The apparatus as claimed in any one of claims 1 to 8, wherein said passageway comprises a capillary extending through said passageway and across said interrogation optical fiber and adapted to channel said fluid and said particle analytes through said passageway.

10. The apparatus as claimed in claim 9, wherein an inside surface and an outside surface of said capillary have a substantially rectangular cross-section.

11. The apparatus as claimed in any one of claims 1 to 10, further comprising a band-pass filtering module located between said light source unit and said passageway.

12. The apparatus as claimed in any one of claims 1 to 11, wherein said interrogation optical fiber comprises a first fiber section located between said input and said passageway and a second fiber section located on an opposite side of said passageway relative to said first fiber section, wherein said first and said second fiber section are dissimilar in at least one of a geometry and an optical property.

13. The apparatus as claimed in claim 12, wherein said first fiber section and said second fiber section are joined on a subregion of their cross-section excluding said passageway.

14. The apparatus as claimed in claim 12, wherein said first fiber section and said second fiber section are partly fusion-spliced together so as to form said passageway in between.

15. The apparatus as claimed in claim 1, wherein said passageway is a hole defined in said interrogation optical fiber.

16. The apparatus as claimed in claim 15, wherein said hole is bored in said interrogation optical fiber using at least one of contact micro-machining, non-contact micro-machining and chemical etching.

17. The apparatus as claimed in any one of claims 1 to 16, further comprising a mirror located at an output of said interrogation optical fiber for reflecting said excitation light back into said interrogation optical fiber.

18. An apparatus for use in analyzing a fluid with particle analytes, the apparatus comprising:
    an interrogation optical fiber having an input optically connectable to a light source for receiving an excitation light, a core extending along a longitudinal axis of said interrogation optical fiber for guiding said excitation light, and a hole extending throughout said interrogation optical fiber in a transverse direction relative to said longitudinal axis of said interrogation optical fiber and traversing said interrogation optical fiber directly through said core for circulating said fluid such that circulating particle analytes cross said excitation light as said excitation light propagates through said hole; and a light collection unit located along said interrogation optical fiber in the vicinity of said hole for collecting light resulting from said interaction of said excitation light with said particle analytes of said fluid.

19. The apparatus as claimed in claim 18, wherein said interrogation optical fiber has a collection surface on its outer cladding surface and in the vicinity of said hole which is one of a flat surface and a surface engraved in said outer cladding surface and which is adapted to collect said light resulting from said interaction of said excitation light with said particle analytes, said light collection unit being disposed adjacent to said collection surface.

20. The apparatus as claimed in claim 19, wherein said collection surface is a surface engraved in said outer cladding surface in the shape of one of a spherical lens, an aspherical lens and a conical lens.

21. The apparatus as claimed in any one of claims 18 to 20, wherein said light collection unit comprises at least one collection optical fiber.

22. The apparatus as claimed in any one of claims 18 to 21, further comprising a mirror located at an output of said interrogation optical fiber for reflecting said excitation light back into said interrogation optical fiber.

23. The apparatus as claimed in any one of claims 18 to 22, further comprising a capillary extending along said hole and across said interrogation optical fiber and adapted to channel said fluid and said particle analytes through said hole.

24. The apparatus as claimed in claim 23, wherein said capillary has a substantially rectangular cross-section.

25. The apparatus as claimed in any one of claims 18 to 24, wherein said core of said interrogation optical fiber has a substantially rectangular cross-section.

26. The apparatus as claimed in any one of claims 18 to 25, wherein said hole has a substantially rectangular shape.

27. The apparatus as claimed in any one of claims 18 to 26, further comprising a band-pass filter positioned between said input of said interrogation optical fiber and said hole.

28. The apparatus as claimed in any one of claims 18 to 27, wherein said interrogation optical fiber has an input optically connectable to a light source unit and wherein said light source unit is a light emitting diode.

29. The apparatus as claimed in any one of claims 18 to 28, wherein a numerical aperture of said interrogation optical fiber and a central wavelength of said excitation light are such that a speckle appearing in said excitation light has a size that is substantially smaller than a size of said particle analytes.

30. A method for analyzing a fluid with particle analytes, the method comprising:

producing a substantially uniform spatial illumination over a cross-section of an optical core of a multimode interrogation optical fiber by injecting an excitation light in said interrogation optical fiber for propagation in said optical core;

exposing each of said particle analytes of said fluid to substantially equal excitation light by channeling said fluid through a passageway extending throughout said interrogation optical fiber and intersecting said optical core of said interrogation optical fiber such that said fluid circulates across said optical core; and detecting a result of an interaction of said excitation light and said particle analytes to determine said parameter to be analyzed.

31. The method as claimed in claim 30, wherein said detecting comprises detecting said result at an output of said interrogation optical fiber.

32. The method as claimed in claim 30, wherein said detecting comprises collecting said result on a side of said interrogation optical fiber in the vicinity of said passageway and in a transversal direction relative to the interrogation optical fiber.

33. The method as claimed in any one of claims 30 to 32, further comprising selecting a numerical aperture of said interrogation optical fiber and a central wavelength of said excitation light such that a speckle appearing in said excitation light has a size that is smaller that a size of said particle analytes.

34. The method as claimed in claim any one of claims 30 to 33, wherein said producing comprises propagating at least 1000 transversal modes of propagation of said excitation light in said optical core of said interrogation optical fiber.

* * * * *